(12) United States Patent
Mansfield

(10) Patent No.: US 9,642,742 B2
(45) Date of Patent: May 9, 2017

(54) EYE DROP APPLICATOR AND DROP TRANSFER METHOD

(71) Applicant: Harold D. Mansfield, Sarasota, FL (US)

(72) Inventor: Harold D. Mansfield, Sarasota, FL (US)

(*) Notice: Subject to any disclaimer, the term of this patent is extended or adjusted under 35 U.S.C. 154(b) by 269 days.

(21) Appl. No.: 13/887,966

(22) Filed: May 6, 2013

(65) Prior Publication Data

US 2014/0094759 A1  Apr. 3, 2014

Related U.S. Application Data

(60) Provisional application No. 61/800,172, filed on Mar. 15, 2013, provisional application No. 61/709,095, filed on Oct. 2, 2012.

(51) Int. Cl.
*A61M 35/00* (2006.01)
*A61F 9/00* (2006.01)
(Continued)

(52) U.S. Cl.
CPC ............. *A61F 9/0008* (2013.01); *A61F 9/00* (2013.01); *A61F 9/0026* (2013.01); *A61M 35/003* (2013.01)

(58) Field of Classification Search
CPC ........ A61F 9/0008; A61F 9/0026; A61F 9/00; A61M 35/003
(Continued)

(56) References Cited

U.S. PATENT DOCUMENTS 2,658,613 A   11/1953  Volckening
3,893,989 A   7/1975   Leicht et al.
(Continued)

FOREIGN PATENT DOCUMENTS

CH   EP1332754 A1   8/2003
EP   11726327 A1    11/2006
(Continued)

OTHER PUBLICATIONS

"Lab Supplies." MidAtlantic Ortho. MidAtlantic Ortho, Aug. 2, 2009. Web. Oct. 1, 2013. <http://www.midatlanticortho.com/lab_supplies.php>.*
(Continued)

*Primary Examiner* — Tatyana Zalukaeva
*Assistant Examiner* — Andrew J Mensh
(74) *Attorney, Agent, or Firm* — George F. Wallace

(57) ABSTRACT

A handheld applicator designed to transfer a liquid drop of ophthalmic medicament into a human eye. The basic structure comprises a finger grip section and a drop retainer section, preferably connected to the grip section with an extension. The device is made from an elastomeric material that will allow for the safe transfer of a liquid drop into the eye. A drop dispensed from a container is placed onto the drop retainer section of the device where the surface tension provides drop adhesion. The user may administer the drop, without having to tilt the head, while maintaining an eyeglass assisted view into a mirror. Application of the drop occurs from the peripheral line of vision. When contact is made to the eye, surface tension is relieved and the drop safely transfers into the eye. The same applicator may have a drop retainer section with a different structure on each side.

16 Claims, 22 Drawing Sheets

(51) Int. Cl.
*A61H 33/04* (2006.01)
*B43M 11/00* (2006.01)
*A46B 11/00* (2006.01)
*B65D 88/54* (2006.01)

(58) Field of Classification Search
USPC ......... 604/295, 298, 302; 222/319; 401/119,
401/128; 422/100; 433/30
See application file for complete search history.

(56) References Cited

U.S. PATENT DOCUMENTS

| | | | |
|---|---|---|---|
| 3,934,585 A | 1/1976 | Maurice | |
| 3,958,528 A * | 5/1976 | Hill | 116/219 |
| 4,002,168 A | 1/1977 | Petterson | |
| 4,036,230 A | 7/1977 | Adams | |
| 4,111,200 A | 9/1978 | Sbarra et al. | |
| 4,113,802 A | 9/1978 | Matteoli et al. | |
| 4,629,456 A | 12/1986 | Edwards | |
| 4,685,906 A | 8/1987 | Murphy | |
| 4,733,802 A | 3/1988 | Sheldon | |
| 4,761,381 A * | 8/1988 | Blatt et al. | 436/165 |
| 4,834,727 A | 5/1989 | Cope | |
| 4,838,851 A | 6/1989 | Shabo | |
| 4,878,775 A | 11/1989 | Norbury et al. | |
| 4,913,682 A | 4/1990 | Shabo | |
| 4,955,745 A | 9/1990 | Vauquelin | |
| 4,973,322 A | 11/1990 | Jewart | |
| 4,997,875 A | 3/1991 | Geddes et al. | |
| 5,007,905 A | 4/1991 | Bauer | |
| 5,040,706 A | 8/1991 | Davis et al. | |
| 5,133,702 A | 7/1992 | Py | |
| 5,221,027 A | 6/1993 | Gibilsco | |
| 5,238,989 A | 8/1993 | Takei et al. | |
| 5,401,259 A | 3/1995 | Py | |
| 5,412,020 A | 5/1995 | Yamamoto et al. | |
| 5,514,118 A | 5/1996 | Kummer et al. | |
| 5,516,008 A | 5/1996 | Rabenau et al. | |
| 5,578,019 A | 11/1996 | Feldman | |
| 5,578,020 A | 11/1996 | Mosley | |
| 5,578,021 A | 11/1996 | Cornish | |
| 5,584,823 A | 12/1996 | Valberg | |
| 5,613,957 A | 3/1997 | Py | |
| 5,614,172 A | 3/1997 | Geimer | |
| 5,630,793 A | 5/1997 | Rowe | |
| 5,665,079 A | 9/1997 | Stahl | |
| 5,678,729 A | 10/1997 | Raymond | |
| 5,685,869 A | 11/1997 | Py | |
| 5,713,495 A | 2/1998 | Menard | |
| 5,756,050 A * | 5/1998 | Ershow et al. | 422/501 |
| 5,810,794 A | 9/1998 | Peplinski | |
| 5,848,999 A | 12/1998 | Basilice et al. | |
| 5,888,005 A | 3/1999 | Gueret | |
| 5,916,953 A | 6/1999 | Jacoby et al. | |
| 5,944,702 A | 8/1999 | Py | |
| 5,976,116 A | 11/1999 | Muroff | |
| 5,997,518 A | 12/1999 | Laibovitz et al. | |
| 6,041,978 A | 3/2000 | Hagele | |
| 6,051,190 A * | 4/2000 | Birch et al. | 422/502 |
| 6,129,236 A | 10/2000 | Hagele | |
| 6,159,189 A * | 12/2000 | Finnemore et al. | 604/294 |
| 6,197,008 B1 | 3/2001 | Hagele | |
| 6,325,784 B1 | 12/2001 | Muroff | |
| 6,331,085 B1 * | 12/2001 | Schrepf et al. | 401/128 |
| 6,472,473 B1 | 10/2002 | Ansems et al. | |
| 6,533,764 B1 | 3/2003 | Haffner et al. | |
| 6,595,970 B1 | 7/2003 | Davidian | |
| 6,632,202 B1 | 10/2003 | Hagele | |
| 6,666,607 B2 | 12/2003 | Gueret | |
| 6,736,802 B1 | 5/2004 | Recanati | |
| 6,869,421 B2 | 3/2005 | Hanley | |
| 7,063,241 B2 | 6/2006 | Spadaa et al. | |
| 7,235,606 B2 | 6/2007 | Spencer et al. | |
| 7,309,329 B2 | 12/2007 | Cress | |
| 7,374,559 B2 | 5/2008 | Berger et al. | |
| 7,503,469 B2 | 3/2009 | Bloom et al. | |
| 7,527,613 B2 | 5/2009 | Gaynes | |
| 7,563,256 B2 | 7/2009 | Hearne | |
| 7,665,923 B2 | 2/2010 | Py et al. | |
| 7,678,089 B2 | 3/2010 | Py et al. | |
| 7,758,553 B2 | 7/2010 | Poisson et al. | |
| 7,846,140 B2 | 12/2010 | Hagele | |
| 7,959,369 B2 | 6/2011 | Gueret | |
| 8,066,682 B2 | 11/2011 | Kimura et al. | |
| 8,496,028 B2 | 7/2013 | Gaudreau et al. | |
| 2002/0016576 A1 | 2/2002 | Lee | |
| 2002/0058914 A1 | 5/2002 | Henniges et al. | |
| 2002/0107492 A1 | 8/2002 | Brach et al. | |
| 2002/0107493 A1 | 8/2002 | Cogger | |
| 2002/0161344 A1 | 10/2002 | Peciat et al. | |
| 2004/0111070 A1 | 6/2004 | Hanley | |
| 2004/0267214 A1 | 12/2004 | Kerssies | |
| 2005/0043693 A1 | 2/2005 | Infantolino | |
| 2005/0049562 A1 | 3/2005 | Cress | |
| 2006/0090725 A1 | 5/2006 | Garvey et al. | |
| 2006/0201976 A1 | 9/2006 | Bloom et al. | |
| 2007/0055208 A1 | 3/2007 | Berger et al. | |
| 2007/0179457 A1 | 8/2007 | Whitmore et al. | |
| 2007/0262096 A1 | 11/2007 | Gaynes | |
| 2007/0282241 A1 | 12/2007 | Squires | |
| 2007/0287123 A1 * | 12/2007 | Swift et al. | 433/30 |
| 2008/0039807 A1 | 2/2008 | Pine | |
| 2008/0145406 A1 | 6/2008 | Ashgarian et al. | |
| 2008/0208148 A1 | 8/2008 | Soon et al. | |
| 2010/0006590 A1 | 1/2010 | Withoos et al. | |
| 2010/0266664 A1 | 10/2010 | Ashgarian et al. | |
| 2010/0286634 A1 | 11/2010 | Marx | |
| 2011/0009836 A1 | 1/2011 | Chebli et al. | |
| 2011/0092889 A1 | 4/2011 | Daniels et al. | |
| 2011/0208136 A1 | 8/2011 | Sollingen | |
| 2012/0150132 A1 | 6/2012 | Cress | |
| 2012/0179122 A1 | 7/2012 | Eilat et al. | |
| 2012/0253300 A1 | 10/2012 | Kaufman | |
| 2012/0310184 A1 | 12/2012 | Pedersen | |
| 2013/0006202 A1 | 1/2013 | Marx | |
| 2013/0030393 A1 | 1/2013 | Bogdan | |

FOREIGN PATENT DOCUMENTS

| | | |
|---|---|---|
| EP | 2181620 A1 | 5/2010 |
| JP | 2004267709 A | 9/2004 |
| JP | 2006020908 A | 1/2006 |
| JP | 2006116071 A | 11/2006 |
| JP | 2009226187 A | 10/2009 |
| JP | 2010029596 A | 2/2010 |
| KR | 10020050000254 | 1/2005 |
| WO | 98/55059 A1 | 12/1998 |
| WO | WO/00/69506 A1 | 11/2000 |
| WO | 03/076000 A1 | 9/2003 |
| WO | 2007/037584 A2 | 4/2007 |
| WO | 2009/120550 A2 | 10/2009 |
| WO | 2011/057363 A1 | 5/2011 |
| WO | 2012/144437 A1 | 10/2012 |

OTHER PUBLICATIONS

Tiwari, Rajkiran, and D.R. Paul. "Polypropylene-elastomer (TPO) nanocomposites." Elsevier: Polymer. 52.21 (2011): 4955-4969. Web. Oct. 3, 2013. <http://www.sciencedirect.com/science/article/pii/S0032386111006859#>.*

Shmulinson, Michal, Mercedes Galan-Fereres, et al. "Formation of Elastomeric Polypropylene Promoted by Racemic Acetylacetonate Group 4 Complexes." Organometallics. 19. (1999): 1208-1210. Web. Oct. 3, 2013. <http://pubs.acs.org/doi/pdf/10.1021/om9908985>.*

"Vistamaxx propylene-based elastomer." ExxonMobil Chemical. N.p., Jan. 29, 2010. Web. Oct. 3, 2013. <http://www.exxonmobilchemical.com/Chem-English/brands/vistamaxx-propylene-based-elastomers.aspx?In=productsservices>.* https://web.archive.org/web/20110220003150/http://eyepodmagic.com/ (Feb. 20, 2011).*

(56) References Cited

OTHER PUBLICATIONS http://www.prnewswire.com/news-releases/inventor-discovers-a-new-way-of-inserting-contact-lens-in-1-second----finger-free-79397202.html.*
http://www.news-medical.net/news/20091211/Hot-Ideas-World-creates-Eye-POD-Eye-Care-Kit.aspx.*
Fraunfelder, Frederick T., "Extraocular Fluid Dynamics: How Best to Apply Topical Ocular Medication," Tr. Am. Ophth. Soc., vol. LXXIV, pp. 457-487 (1976).
Winfield, A. J. et al., "A Study of the Causes of Non-compliance by Patients Prescribed Eyedrops," British Journal of Ophthalmology, vol. 74, pp. 477-480 (1990).
Salyani, Aasif, et al., "Evaluation of an eye drop guide to aid self-administration by patients experienced with topical use of glaucoma medication," Can. J. Opthalmol., vol. 40, pp. 170-174 (Oct. 13, 2004).
Bouteau, Murielle et al., "Sliding Behavior of Liquid Droplets on Tilted Langmuir-Blodgett Surfaces," Journal of Colloid and Interface Science, vol. 317, pp. 247-254, (Sep. 20, 2007), (c) Elsevier Inc.
Tsai, Tony et al., "An Evaluation of How Glaucoma Patients Use Topical Medications: A Pilot Study," Trans. Am. Ophthalmol. Soc., vol. 105, pp. 29-35 (2007).
Parkkari, Minna, et al., "Handling Test of Eye Drop Dispenser—Comparison of Unit-Dose Pipettes with Conventional Eye Drop Bottles," Journal of Ocular Pharmacology and Therapeutics, vol. 26, No. 3, pp. 273-276 (2010). (c) Mary Ann Liebert, Inc.
Connor, A. J. et al., "Force requirements in topical medicine use—the squeezability factor", Eye, vol. 25, pp. 466-469, (Feb. 4, 2011), (c) Macmillan Publishers Limited.
Newsom, Richard, "How to Put in Eye Drops—Patient Information," Mar. 2008 [online], [retrieved on Apr. 23, 2013]. Retrieved from the Internet <URL:http://www.rbnewsom.plus.com/patient/21%20How%20to%20put%20in%20Eye%20Drops.pdf>.
National Institutes of Health Clinical Center, "How to Put in Your Eye Drops," Jun. 2008 Publication [online], [retrieved on Oct. 25, 2012]. Retrieved from the Internet <URL:http://www.cc.nih.gov/ccc/patient_education/pepubs/eyedrops.pdf>.
Glaucoma Research Foundation, "Eye Drop Tips," May 2012 Issue of Gleams [online], [retrieved on Oct. 25, 2012]. Retrieved from the Internet <URL:http://www.glaucoma.org/treatment/eyedrop-tips.php.
Robin, Alan, "Glaucoma Eye Drops: Suggestions on Use," Jan. 2012 Issue of Gleams [online], [retrieved on Oct. 25, 2012]. Retrieved from the Internet <URL:http://www.glaucoma.org/treatment/glaucoma-eye-drops-suggestions-on-use.php>.
"Silbione(R) Liquid Silicone Rubbers for Healthcare," data sheet (Nov. 2010), Bluestar Silicones USA, East Brunswick, NJ.
Santoprene(TM) 8211-35 Data Sheet (2013), ExxonMobile Chemical, [online], [retrieved on May 15, 2013], Retrieved from the Internet, <URL http://exxonmobilchemical.ides.com/en-US/ds74468/Santoprene%E2%84%A2%208211-35.aspx?I=74710&U=1>.
Vistamaxx(TM) 6102 Data Sheet (2013), ExxonMobile Chemical, [online], [retrieved on May 15, 2013], Retrieved from the Internet, <URL http://exxonmobilchemical.ides.com/en-US/ds114451/Vistamaxx%E2%84%A2%206102.aspx?I=74710&U=1>.
CPT C-Flex(R) R70-046 Data Sheet (2013), Compagnie de Saint-Gobain, [online], [retrieved on May 15, 2013], Retrieved from the Internet, <URL http://www.matweb.com/search/datasheet_print.aspx?matguid=635d37d6dc7d4e07831d71b31e6e2ad3>.
Enflex S4065A Natural Data Sheet (Jul. 12, 2011), Ravago Manufacturing Americas/Entec Polymers, LLC, Orlando, Florida.
Hytrel(R) 3078 Product Information (May 2013), Dupont, (May 2013), [online], [retrieved on May 15, 2013], Retrieved from the Internet, <URL http://catalog.ides.com/Datasheet.aspx?I=95947&U=1&FMT=PDF&E=61060>.

"Wetting." Wikipedia: The Free Encyclopedia. Wikimedia Foundation, Inc. Apr. 11, 2013. [online], [retrieved on May 24, 2013], Retrieved from the Internet, <URL http://en.wikipedia.org/wiki/Wetting>.
"Polymer." Wikipedia: The Free Encyclopedia. Wikimedia Foundation, Inc. May 26, 2013. [online], [retrieved on May 28, 2013], Retrieved from the Internet, <URL http://en.wikipedia.org/wiki/Polymer>.
"Thermoplastic elastomer." Wikipedia: The Free Encyclopedia. Wikimedia Foundation, Inc. May 17, 2013. [online], [retrieved on May 24, 2013], Retrieved from the Internet, <URL http://en.wikipedia.org/wiki/Thermoplastic_elastomer.
"Adhesion." Wikipedia: The Free Encyclopedia. Wikimedia Foundation, Inc. Apr. 11, 2013. [online], [retrieved on May 28, 2013], Retrieved from the Internet, <URL http://en.wikipedia.org/wiki/Adhesion>.
"Primer: Hygroscopic vs. Non-Hygroscopic Resins," Plastics Technology Magazine, (2013), [online], [retrieved on May 24, 2013], Retrieved from the Internet, <URL http://www.ptonline.com/knowledgecenter/Plastics-Drying/Resin-Types/Hygroscopic-VS-Non-Hygroscopic-Resins>.
"Drying Plastics," Steinwall, Inc. (2012) [online], [retrieved on May 24, 2013], Retrieved from the Internet, <URL http://www.steinwall.com/ART-drying-plastics.html>.
"Adhesion and Cohesion of Water," USGS Water Science School, (Jan. 10, 2013) [online], [retrieved on May 24, 2013], Retrieved from the Internet, <URL http://ga.water.usgs.gov/edu/adhesion.html>.
"Surface Tension and Water," USGS Water Science School, (Jan. 10, 2013) [online], [retrieved on May 24, 2013], Retrieved from the Internet, <URL http://ga.water.usgs.gov/edu/surface-tension.html>.
"Surface Tension, Surface Energy, Contact Angle and Adhesion," PRA, a Pera Technology company, (2013) [online], [retrieved on May 24, 2013], Retrieved from the Internet, <URL http://www.pra-world.com/technical_services/laboratory/testing/surface-tension>.
"Capillary action," thefreedictionary.com (Houghton Mifflin Company), (2009) [online], [retrieved on May 24, 2013], Retrieved from the Internet, <URL ) http://www.thefreedictionary.com/p/capillary%20action>.
"Surface tension," thefreedictionary.com (Houghton Mifflin Company), (2009) [online], [retrieved on May 24, 2013], Retrieved from the Internet, <URL http://www.thefreedictionary.com/p/surface%20tension>.
"Cohesive force," thefreedictionary.com (Houghton Mifflin Company), (2009) [online], [retrieved on May 24, 2013], Retrieved from the Internet, <URL http://encyclopedia.thefreedictionary.com/p/Cohesive%20force>.
Bales, Steven J., "Surface Finish: Understanding Mold Surface Lingo," Mold Making Technology (Jan. 1, 2009) [online], [retrieved on May 24, 2013], Retrieved from the Internet, <URL http://www.moldmakingtechnology.com/articles/surface-finish-understanding-mold-surface-lingo>.
"Diamond Mold Polishing & Finishing," Bales Mold Service, Inc., (2009) [online], [retrieved on May 24, 2013], Retrieved from the Internet, <URL http://www.balesmold.com/diamondpolishing.htm>.
"Accelerated Aging Calculator," Medical Package Testing, div. of Life Science Outsourcing, Inc. [online], retrieved on May 24, 2013], Retrieved from the Internet, <URL http://lso-inc.com/medical-packaging-testing/accelerated-aging.html>.
Alan N. Gent. "elastomer" Encyclopedia Britannica: Encyclopedia Britannica Online. Encyclopedia Britannica Inc., 2013. Web.Aug. 21, 2013 [online], [retrieved on Aug. 21, 2013]. Retrieved from the Internet <http://www.britannica.com/EBchecked/topic/1820881/elastomer>.
Zeus Industrial Products, Inc. Zeus Technical Newsletter: Strength & Stiffness of Plastics. Copyright 2005-2010 Zeus Industrial Products, Inc. [online], [retrieved on Aug. 19, 2013]. Retrieved from the Internet <URL:http://www.zeusinc.com/UserFiles/zeusinc/.../Zeus_StrengthStiffnessPlastics.pdf.
Smooth-On, Inc., Easton PA 18042S, "Durometer Shore Hardness Scale," Char Extract, Copyright 2008 Smooth-On, Inc. [online],

(56) References Cited

OTHER PUBLICATIONS

[retrieved on Aug. 28, 2013]]. Retrieved from the Internet <URL:http://http://www.smooth-on.com/index.php?cPath=1370.
Granta Design Limited, Cambridge, UK, Chart 1: Young's Modulus, E, and Density, ro (extract), copyright 2009, [online], [retrieved on Aug. 28, 2013]. Retrieved from the Internet <http://www.me.uprm.edu/vgoyal/inme4011/Online_inme4011/Topic2_MaterialSelection/AshbyCharts.pdf>, scroll down to chart 1 on p. 7.
Bluestar Silicones USA Corp, East Brunswick, NJ 08816-1100, "Sales Specifications" for SILB LSR 43XX, dated Sep. 3, 2013.
Eye*POD website documents, Hot Ideas Magic, Inc., [online], [retrieved on Aug. 1, 2013], Retrieved from the Internet, <URL http://www.eyepodmagic.com>, 10 pages on 22 sheets.
Eye*POD(R), S/N 77920915, Courtenay, Charles R., [online], [retrieved on Aug. 1, 2013], Retrieved from the Internet, <http://tess2.uspto.gov/bin/gate.exe?f=doc&state=4802:7jqtje.2.1>.
"Eye* POD (Eye Discovery & Eye Doctors)", Courtenay, Dr. C. R., Jul. 30, 2013 (Private Communication), 2 pages on 2 sheets.

\* cited by examiner

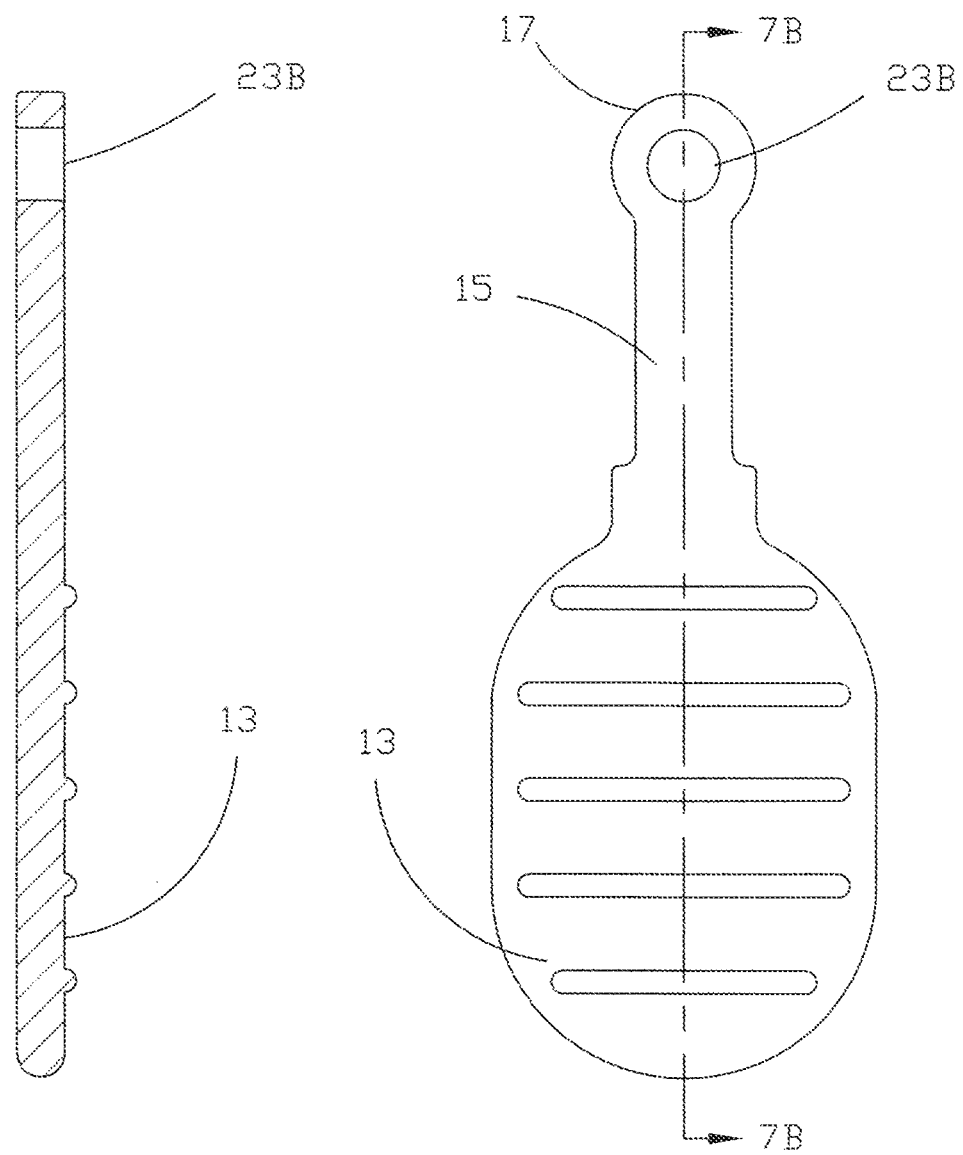
FIG. 7B                    FIG. 7A

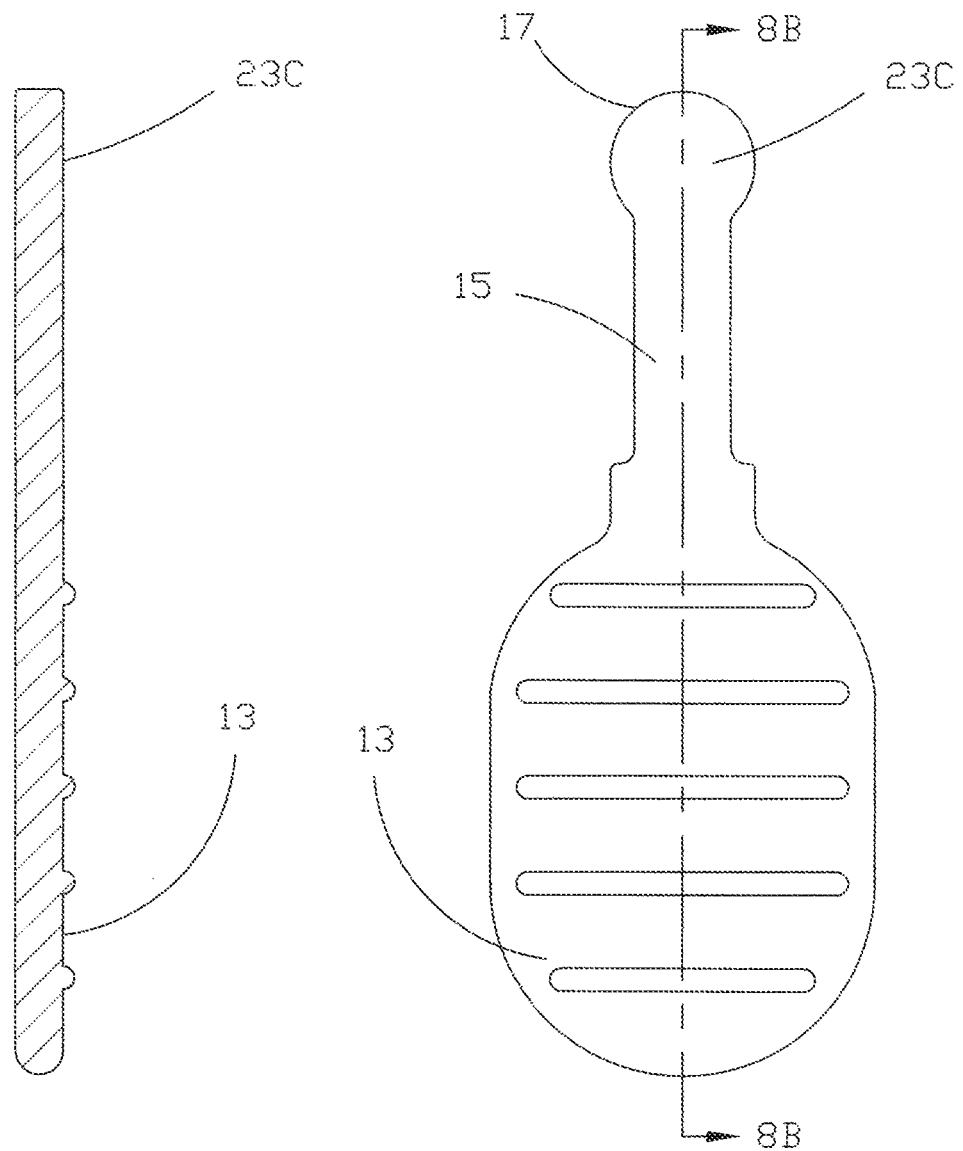

EYE DROP APPLICATOR AND DROP TRANSFER METHOD

CROSS REFERENCE TO RELATED APPLICATIONS

This application claims the benefit of U.S. provisional application Nos. 61/709,095, filed Oct. 2, 2012, and 61/800,172, filed Mar. 15, 2013, both of which are incorporated herein by reference in their entirety.

BACKGROUND

1. Technical Field

The invention relates to manually applying drops to human eyes, more particularly, a manual eye drop applicator and a method to insert a drop of liquid into the eye.

2. Background

Using eye droppers to insert drops into an eye to alleviate various conditions has been known for a long time. The human eye is subject to several maladies, some of which can be treated with the topical application of medicaments. For example, bacterial conjunctivitis, a/k/a "pink eye" (as opposed to the viral form) can be treated with antibacterial solutions. Keratoconjunctivitis sicca, a/k/a "chronic dry eyes" can be ameliorated with artificial tears. Various eye irritations can be treated with artificial tears or other solutions.

In these cases, the object is to get at least some of the solution into the lower conjunctival sac, the space between the sclera and lower eye lid. Since the solutions are not expensive, wasted drops that run down the check are not a major concern.

A much more serious affliction is glaucoma. In the most common forms, this manifests as a buildup of pressure inside the eye between the lens and retina. If left untreated, the optic nerve can be damaged leading to eventual blindness. The usual treatment is to apply one or more medicaments in the form of eye drops. In this case, the cost of wasted drops can become significant. Moreover, prescriptions are based on an assumed dosage of one drop per application and wastage may require premature prescription renewal. Insurance coverage can be an issue. Lastly, most glaucoma medicines have side effects and inadvertent overdosing, though usually limited by conjunctival sac capacity, is not desirable.

Over the counter solutions are generally used on an as needed basis to alleviate a condition that is perceived by the user. Successful drop application often provides some immediate relief. In the case of glaucoma, the drops do not provide any felt relief. However, to prevent further loss of vision, they must be applied two or more times every day for life.

Over the years, a preferred method has been developed for patient administration of medicated drops. Some time ago, bottles with separate glass eye droppers gave way to integral plastic bottles. These are small hand held pliable containers with cone shaped nozzles of varying inner diameters. Inverting the container and squeezing it causes drops to come out. The size of the drop depends on the solution, nozzle diameter and bottle tilt angle.

"How to put in your eye drops" from the NIH Clinical Center is typical patient advice: 1) wash hands to prevent eye infections, 2) hold the bottle in one hand (the right for right-handed people), 3) either lie down or tip the head back so the eye is looking up, 4) use the index finger of the other hand to pull down the lower lid to form a pocket, and 5) hold the bottle over the eye and squeeze so that a drop falls onto the eye.

While this seems straightforward, it is difficult for a large number of patients to perform consistently well. Most people have a blink reflex which makes it difficult to keep the eye open when viewing a close-in object. Glaucoma generally affects those of advanced age. Often, their manual dexterity is compromised making it hard for them to squeeze out a single drop of an appropriate size, if they can do so at all. Aiming the bottle so that a drop falls into the eye instead of on an eyelid or cheek is a problem for some. As a result, studies have shown that noncompliance with prescribed treatments has proven to be a significant obstacle to effective glaucoma management.

For example, Winfield et al. (1990) undertook a study of the causes of non-compliance and reviews the findings of earlier teams (footnoted) between 1982 and 1986. Problems include missed doses, inability to place drops in eyes, a wide variation in drop size from commercial droppers, and difficulty in aiming. Several aids are mentioned that were available in 1985, generally directed to aiming. This study enrolled patients (ages 9-92) taking drops for glaucoma (32%), post-surgical (25%), dry eyes (10%), irritation (10%), balance other. Administration was by means of a dispenser bottle aimed at the eye. They found that 57% had some difficulty, poor aim being the major problem with difficulty squeezing the bottle and blinking next. The authors proposed a bottle holding appliance with a stabilizer surrounding the eye socket.

Although not a compliance study, problems were apparent even earlier. Fraunfelder (1976) used radioactive technetium as a tracer to study the fluid dynamics of applied topical medication to determined how best to apply it. He notes that commercial eyedroppers produce 50-75 uL drops and are much too large, since they produce a blink reflex which washes away most of it. Based on what the conjunctival sac can hold after blinking, a drop size of 13 uL is recommended.

Salyani et al. (2005) stated that "Methods to improve patient compliance with prescribed topical use of glaucoma medication are sorely needed." They evaluated patient use of a three part eye drop guide comprising a transparent plastic inverted funnel that fit over a bottle. Apparently, it proved difficult to wash and was not worth the effort for experienced users. Newsom (2008), in his advice on How to Put in Eye Drops, states that "many people find taking drops difficult," but shows two drop aids. Xalease and Opticare appear to be combination bottle squeezer and eye socket alignment guides.

The problem is still not solved. Connor & Severn (2011), in a study of bottle force requirements, summarize earlier studies: "Non-compliance in glaucoma and ocular hypertension is common." "At least 50% of patients report difficulty in self-administration. The two most common frequently reported causes of difficulty include aiming a bottle and squeezing a bottle." Currently, they opine: "The insidious nature of disease progression and necessity for long-term therapy are key issues. In these conditions, the ease of topical delivery is of paramount importance."

Thus, it is clear that, for a very long time, there has been a desperate need for an advance over an eyedropper bottle.

Some patents have also addressed similar problems. Below are uncritical thumbnail sketches using the inventor's terminology as much as possible in approximate date order. Even if some of these patents are not analogous art, they do provide a historical perspective. Of course, searching is not foolproof and there may be other more relevant patents not found or inadvertently glossed over.

U.S. Pat. No. 4,036,230 to Adams on Jul. 19, 1977, titled, "Medicinal Insert Instrument," is concerned with a swab-like device that places and removes plastic inserts that provide timed-release medication to the eye.

U.S. Pat. No. 4,913,682 to Shabo on Apr. 3, 1990 (Division of U.S. Pat. No. 4,838,851, Jun. 13, 1989), titled, "Applicator and Package Thereof," compromises a handle and an absorbent tip for scrubbing an eyelid.

U.S. Pat. No. 5,040,706 to Davis et al. on Aug. 20, 1991, titled, "Liquid Drop Dispensing Apparatus," comprises a hollow compressible body connected to a nozzle at approximately 90°. The nozzle discharge passage is sized to produce a liquid drop of predetermined size when the body is squeezed. Advantages include not having to tilt the head back and being able to use one hand to hold the lower eyelid down while squeezing the body with the other.

U.S. Pat. No. 5,516,008 to Rabenau et al. on May 14, 1996, titled, "Medication Dispensing Container," replaces the conventional squeeze bottle with a small capacity storage cavity having a flexible top wall which can be squeezed. A discharge nozzle is at an approximately right angle to the cavity housing body. Problems overcome include sterilization and plastic manufacturing which can result in rough edge eye hazards.

U.S. Pat. No. 5,888,005 to Gueret on Mar. 30, 1999, titled, "Capillary Dosing unit with Terminal Slit," is directed to the unrelated field of applying dermopharmaceuticals to the nails, eyelids, or other parts of the face or scalp. A flexible hand-held applicator has a cylindrical end with a slit along a diameter that acts as a capillary reservoir after dipping into a solution. Dosing depends on capillary volume since excess can be wiped off inside a dispenser bottle.

U.S. Pat. No. 5,665,079 to Stahl on Sep. 9, 1997, titled, "Eye Drop Dispenser Including Slide," provides a slide to which a conventional eye drop squeeze bottle may be attached. Drops squeezed into a channel on the slide roll into the eye. This allows upright application and overcomes the blink reflex of an overhead bottle.

U.S. Pat. No. 6,041,978 to Hagele on Mar. 28, 2000, titled, "Liquid Dropper for Upright Eye Drop Instillation," comprises a squeeze bottle reservoir with a conduit having a delivery end at right angles to the squeeze bottle axis. Inside the conduit, is a rod which culminates in a ball that collects liquids from the conduit forming drops that fall into the eye. The major problem solved is to allow the head to remain upright without the drawbacks of the prior art which did not well direct drops into the eye.

U.S. Pat. No. 6,869,421, issued to Hanley on Mar. 22, 2005, titled, "Device for Non-Gravity Presentation of Liquid Droplet." Liquid is held in a squeeze bottle that communicates via one or more capillary tubes to an eye presentation surface. Drops on the presentation surface are held in place by liquid in the capillary until the device is tilted past some critical angle, at which point the drop is no longer retained on the presentation surface. It is averred that the critical angle may be 90° if several capillary tubes are used.

U.S. Pat. No. 7,374,559 to Berger et al. on May 20, 2008, titled, "Hand-held Device Enabling Accurate Dispensing of a Drop of Liquid into the Eye of a Subject," comprises a funnel connected via a curving capillary tube to a discharge outlet.

U.S. Pat. No. 7,527,613 to Gaynes on May 5, 2009, titled, "Therapeutic Solution Drop Dispenser," proposes a reservoir and a dispensing tip, having various features including removable apertures, at a non-zero angle, theta, to the reservoir portion. It is averred that the dispenser allows keeping the head upright with the dispenser portion horizontal. Apparently, one problem is that prior art drop size depended on the angle of administration. The dispenser tip apertures allow control of drop size in the range of 1 µL to 50 µL.

U.S. Pat. No. 7,846,140 to Hagele on Dec. 7, 2010, titled, "Mini Eye Drop Tip," proposes attaching a mini tip dispenser to existing eye dropper bottles to produce a drop that is smaller than typical. The tip is flexible to prevent eye damage on accidental contact.

Japanese published application, P2006-116071A on May 11, 2006 by Tsubota, titled, "Instrument for Administering an Ophthalmic Drug," relates to administering medicine in the form of solid or semi-solid ointments to an inner eyelid, apparently by an ophthalmologist, to treat dry eye. A spatula-like instrument with a long narrow body and a drug support part with a depression at one end is disclosed. Many materials may be used in construction, but glass or hard plastic is especially preferred, albeit with a rounded end to prevent accidental damage to the cornea. According to the inventor, it is difficult to use a liquid drug with high fluidity or volatility.

As far as is known, none of the inventions related to applying liquid drops to the eye have met with commercial success. The majority of patients are still stuck using an eye dropper bottle with its attendant difficulties.

SUMMARY OF THE INVENTION

The invention solves the problem of getting drops from a bottle into a human eye by using a hand held intermediate transfer device which retains applied drops until the device transfers them by making contact to the eye. Preferably, the device transfers substantially all of the applied drops. Necessarily, the device must be, in part, flexible enough to not damage the eye in normal use.

In one aspect, the present invention is a hand held transfer device that acquires a liquid drop from any type of eye drop dispenser. The specifically designed geometrical shape, material, and surface modifications help to form a liquid drop and induce adhesion for transfer onto the end user's eye. Surface tension and adhesion of the liquid drop will allow the end user to hold the transfer device in any position for transfer of the drop onto the eye. The transfer device is a simple injection molded one piece construction made from a soft elastomeric material. The material is soft and pliable enough to allow for performance characteristics and prevent injuries from inadvertent contact with the end user.

In a preferred version, the transfer device is substantially flat with a finger grip section and an extension connected to a drop retainer portion. Preferably, the finger grip section is wider than the drop retainer portion and the extension narrows in making a transition. Preferably, the drop retainer portion comprises a flat section having a circular end. Circular end size is selected to be optimized for different drop sizes.

To aid in gripping, vertical ridges may be added.

Suitable materials for injection molding include soft and pliable elastomeric polymers ranging from 30 Shore A to 30 Shore D in hardness.

In another aspect, the present invention provides for a protective sheath to store the transfer device during non-use. The transfer device slips into the protective sheath and is secured by friction fit geometry. The sheath may have a color contrasting with the transfer device to allow for a visual cue between the items. The sheath can also be a simple injected molded, one-piece construction made from any semi-ridged thermoplastic material.

In a further aspect, the present invention provides for an adhesive strip on one side of the sheath to allow a supplier or end user to bond the sheath and transfer device to a liquid drop container.

In a still further aspect, the present invention provides a method of liquid drop transfer from any eye drop dispenser container to the transfer device and then to eye of a user without the need to tilt the head so the eye can look up. A mirror can be used as an aid and glasses can be worn if desired.

The preferred method simply requires (with selection of appropriate hands understood depending on which eye): 1) holding the drop transfer device in one hand and squeezing a drop from the container with the other hand onto the top of the drop adhesion structure, 2) pulling down a lower eyelid to expose a lower conjunctival sac, 3) rotating the device by 90° so the drop points to the user, and 4) bringing the device up to the eye and gently touching any part of the cornea or conjunctiva so that surface tension holding the drop to the transfer device is destroyed and the drop wicks off into the conjunctival sac or environs.

Advantageously, the method can be further modified to make it easier. First, since the container is not being squeezed over an upturned head, the squeezing hand/arm can be steadied on a support above a table, for example. The method can be modified to avoid having the device in a direct line of sight by bringing it in from the side. Use of a mirror is also contemplated. In that case, depending on lens coverage, glasses may be left in place.

Methods of liquid drop transfer are, of course, not limited to self-administration; an assistant can help with any or all steps.

BRIEF DESCRIPTION OF VIEWS OF THE EMBODIMENTS

These and other aspects of the invention will become better understood in view of inter alia, the drawings listed below. Many drawings include dimensions so that plastic molds can be made without undue experimentation and meet the best mode requirement. Except for FIGS. 3A-5B, drawings of parts are to an original scale of about 4:1. The dimensions may be used to determine actual scale on reproductions.

FIG. 1A is a top plan view of an eye drop applicator;
FIG. 1B is a sectional view taken along line 1B-1B in FIG. 1A;
FIG. 2A is a top plan view of the eye drop applicator shown in FIG. 1A, drawn to scale and with dimensions added for a working example;
FIG. 2B is a sectional view taken along line 2B-2B in FIG. 2A;
FIG. 3A is a side elevation view of a protective sheath for use with an eye drop applicator;
FIG. 3B is an end view of the sheath shown in FIG. 3A;
FIG. 3C illustrates the sheath in FIG. 3A installed on an applicator;
FIG. 3D is an end view of an enlargement of the applicator to create a friction fit for the sheath in FIG. 3A;
FIG. 4A illustrates how to deposit a drop of fluid on the eye drop applicator shown in FIGS. 1A and 1B;
FIG. 4B illustrates the applicator with a drop adhering to a distal end;
FIG. 4C illustrates the applicator turned 90° and the drop still adhering;
FIG. 4D illustrates the applicator turned up-side down and the drop still adhering;
FIG. 5A illustrates how to transfer drop of fluid to a conjunctival sac of an eye;
FIG. 5B illustrates the same as in FIG. 5A for a person wearing eyeglasses;
FIGS. 6A-9B illustrate four initial liquid silicone rubber versions of the eye drop applicator wherein:
FIG. 6A is a top plan view of a first initial liquid silicone rubber eye drop applicator version;
FIG. 6B is a sectional view taken along line 6B-6B in FIG. 6A;
FIG. 7A is a top plan view of a second initial liquid silicone rubber eye drop applicator version;
FIG. 7B is a sectional view taken along line 7B-7B in FIG. 7A;
FIG. 8A is a top plan view of a third initial liquid silicone rubber eye drop applicator version;
FIG. 8B is a sectional view taken along line 8B-8B in FIG. 8A;
FIG. 9A is a top plan view of a fourth initial liquid silicone rubber eye drop applicator version;
FIG. 9B is a sectional view taken along line 8B-8B in FIG. 9A;
FIGS. 10A-15D, illustrate 26 additional "embodiments" which means at least one side of a two sided device made for testing even though all but the first two embodiments are on the same device and have drawings with some overlap, wherein:
FIG. 10A is a top plan view of embodiment no. 1;
FIG. 10B is a sectional view taken along line 10B-10B in FIG. 10A;
FIG. 11A is a top plan view of embodiment no. 2;
FIG. 11B is a sectional view taken along line 11B-11B in FIG. 11A;
FIG. 12A is a top plan view of embodiment no. 3;
FIG. 12B is a sectional view taken along line 12B-12B in FIG. 12A;
FIG. 12C is a top (bottom of embodiment no. 3) plan view of embodiment no. 4;
FIG. 12D is sectional view taken along line 12D-12D in FIG. 12C;
FIG. 13A is a top plan view of embodiment nos. 5, 7, 9, 11, 13, 15, 17, & 19;
FIG. 13B is a sectional view taken along line 13B-13B in FIG. 13A;
FIG. 13C is a top (bottom of embodiment nos. 5, 7, 9, 11, 13, 15, 17, & 19) plan view of embodiment nos. 6, 8, 10, 12, 14, 16, 18, & 20;
FIG. 13D is sectional view taken along line 13D-13D in FIG. 13C;
FIG. 14A is a top plan view of embodiment nos. 21 & 23;
FIG. 14B is a sectional view taken along line 14B-14B in FIG. 14A;
FIG. 14C is a top (bottom of embodiment nos. 21 & 23) plan view of embodiment nos. 22 & 24;
FIG. 14D is sectional view taken along line 14D-14D in FIG. 14A;
FIG. 15A is a top plan view of embodiment no. 25;
FIG. 15B is a sectional view taken along line 15B-15B in FIG. 15A;
FIG. 15C is a top (bottom of embodiment no. 25) plan view of embodiment no. 26;
FIG. 15D is sectional view taken along line 15D-15D in FIG. 15A;

DETAILED DESCRIPTION

Figures 1A, 1B:
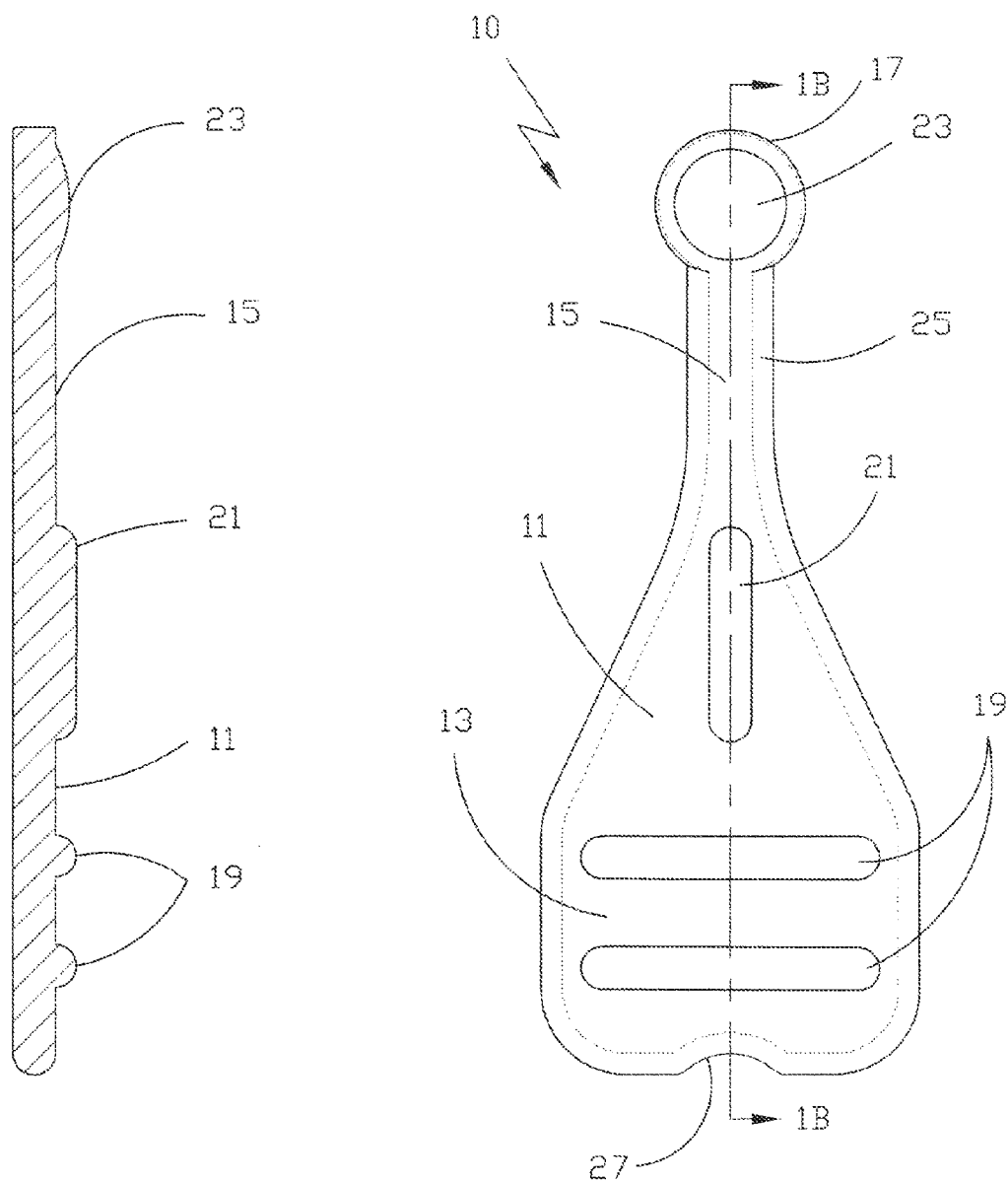

Making the invention will now be described with reference to a working example and FIGS. 1A-2B. FIG. 1A shows a top plan view of an example of the invented eye drop applicator 10. A corresponding sectional view is shown in FIG. 1B with like numerals used for like structural elements. In this example, the applicator has a body 11 of sensibly constant thickness. This is divided into three main sections with additional structure: a finger grip section 13, an extension 15, and a drop retainer portion 17. To assist in manually grasping the applicator, ribs 19 are provided. Rib 21 may further assist and provide a tactile feel for the center of the applicator 10. The spherical bump or dome 23 is more generally a drop adhesion structure whose use will be explained in detail below. A less critical detail is the rounded bevel 25 around the edge of the applicator. The concave indent 27 represents a manufacturing artifact which typically occurs when using an injection molding process.

Figures 2A, 2B:
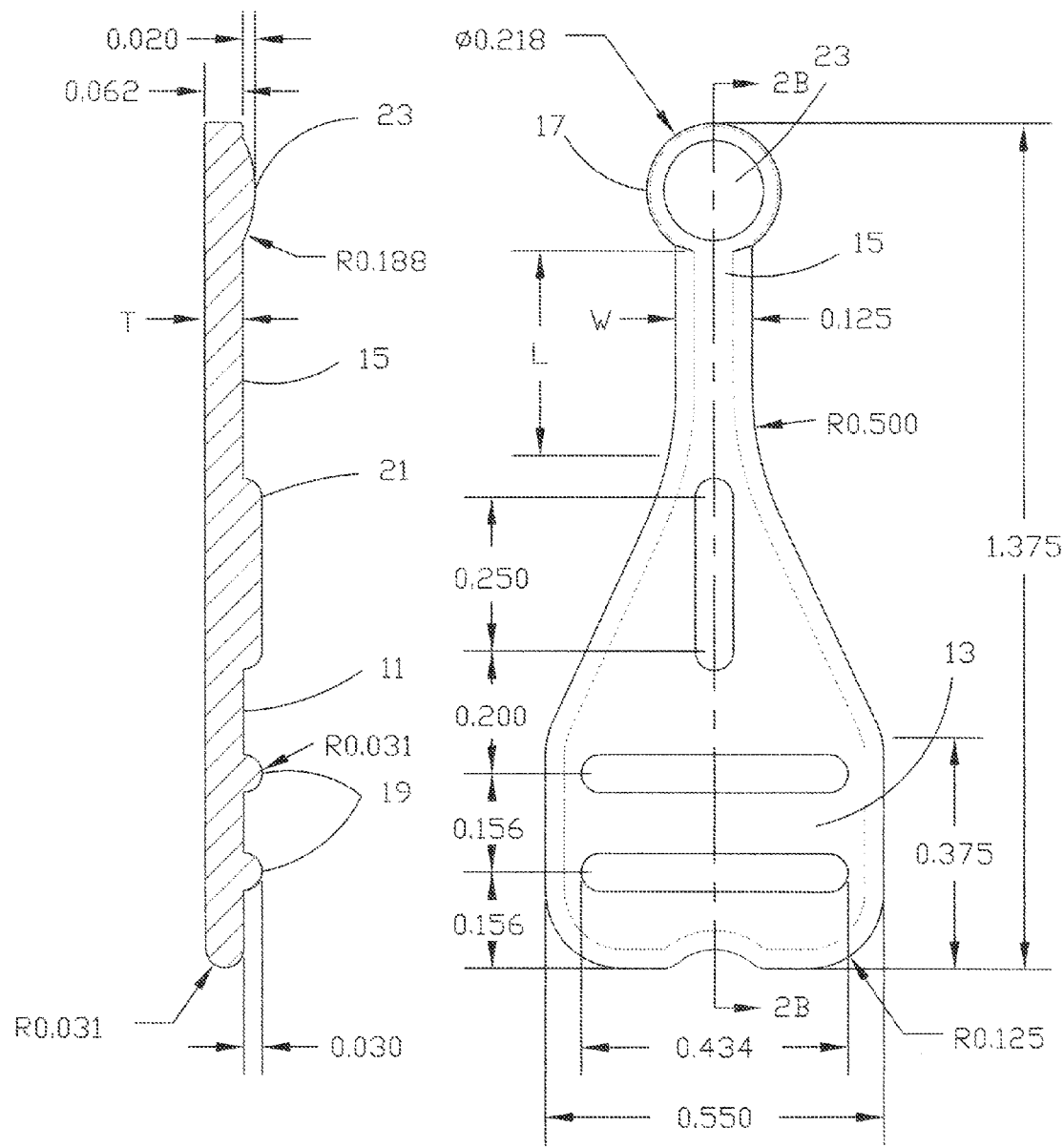

FIGS. 2A and 2B are corresponding scale drawings with dimensions in inches of the working example illustrated in FIGS. 1A and 1B. (As is customary, these are derived from CAD/CAM drawings based on designing with fractional inches where the indicated precision is far more than necessary to produce working parts.) The original scale is 4:1 but the overall width of 0.550 in. (14 mm) and length of 1.375 in. (49 mm) can be used to measure reproductions that do not maintain the same scale. These dimensions represent the best mode for this working example. Some dimensions are more important than others. In particular, the spherical bump or dome 23 has a radius of 0.188 in. (4.8 mm) and is cut off so that it protrudes 0.020 in. (0.5 mm) above the body 11. The purpose of this structure is to retain a drop of fluid by adhesion.

The extension 15 has, where indicated, a thickness T, overall width W, and nominal length L. In this example, the dimensions are T=0.062 in. (1.6 mm), W=0.125 in. (3.2 mm), and L=0.325 in. (8.3 mm). Since the applicator 10 may come into contact with the eye, it is important that, at least the extension 15, is pliable and not too stiff. One measure of pliability is the deflection of the extension section 15 when a force is applied, assuming the finger grip section 13 is held fairly rigidly. From mechanical engineering handbooks, the deflection, d, of a beam fixed at one end per unit of force, F, is $d/F=(L^3)/(3*E*I)$ where L=length of the beam, E=modulus of elasticity (Young's modulus) and I is the moment of inertia for a beam cross section, assumed uniform. For a simple rectangular beam of width, W, and uniform thickness, T, $I=W*T^3/12$, so that $d/F=(4/E*W)*(L/T)^3$. The utility of this somewhat idealized equation (especially when candidate materials do not have a well-defined Young's modulus) is not in designing a first working example but, starting with a working example that is satisfactory, being able by adjusting dimensions, to find approximate equivalents with materials having different moduli, E, or, more readily, changing one dimension and adjusting the others to maintain the same pliability.

An additional possible feature relates to setting the applicator on a surface. In this example, the height of the ribs 19 and 21 above the body 11 is 0.030 in. (0.8 mm). Since this is greater than the 0.020 in. (0.5 mm) height of the spherical dome 23, the applicator 10 can be placed rib and dome side down on a flat surface with the spherical dome suspended above it. At least, before or after use when the applicator is dry, contamination should be reduced.

Prototype working examples were constructed with liquid silicone rubber (LSR) using an injection molding process that cures a two part solution at approximately 400° F. to cause vulcanization. Both the material and the process are well known in the art for making prototypes as well as production quantities and has found wide acceptance for making medical devices. Other thermoplastic elastomers could also be considered.

LSR comes in different formulations having different stiffness properties after vulcanization. The Young's modulus of rubber is non-linear and typically in the range of 0.01 to 0.1 GPa. However, traditionally, LSR formulations are specified by cured hardness in terms of a nominal Shore A Durometer. Available durometers range from 10 to 70 but, based on experience and not any calculations, 40 was selected with good results as describe below.

The molds had a surface finish somewhere between the Society of the Plastics Industry (SPI) gauges A-3 to B-1, about 2 to 4 micro-inches (50 to 100 nm) average roughness.

Figure 3B:
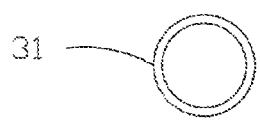
Figure 3A:
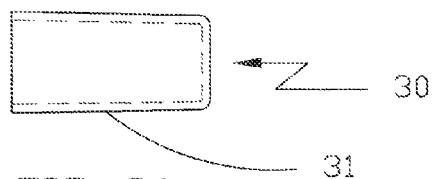
Figure 3C:
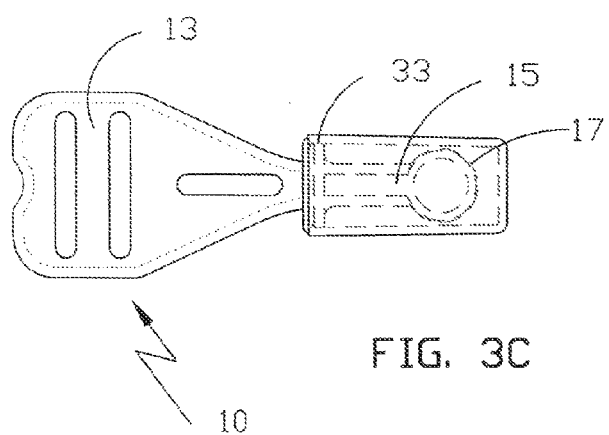
Figure 3D:
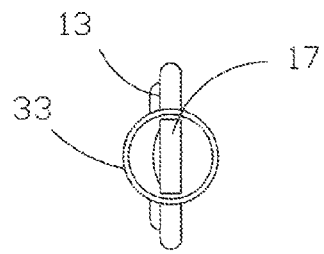

The invention additionally contemplates (prophetically) preventing contamination during storage and non-use. The flexible extension 15 and drop retainer portion 17 sections of the applicator 10 could be protected from contamination using a protective sheath 30 as illustrated in FIGS. 3A-3D. The sheath, shown in FIG. 3A, would be an open-ended tube 31 which, for simplicity could have a round cross-section, as illustrated in FIG. 3B, of suitable size to cover the two sections 15 & 17 of the applicator 10, as illustrated in FIG. 3C. A circular enlargement 33 could be molded onto the applicator 10 to provide a friction fit for the protective sheath 31. FIG. 3D is an end view of the applicator 10 with a molded friction fit enlargement 33. It may be advantageous to use contrasting colors between the sheath 31 and the applicator 10 to make handling more certain.

A method of using the applicator 10 to insert drops in the eye can be described with the aid of FIGS. 4A-5B. Currently, most eye drop medication is supplied in squeezable plastic bottles with a semi-permanent top having a small nozzle. The prior art assumption is that this will be used to insert one or more drops into an eye as discussed in the Background section along with the shortcomings of that method. The current invention overcomes prior art shortcomings by using the applicator 10 as an intermediate eye drop transfer device.

Figure 4A:
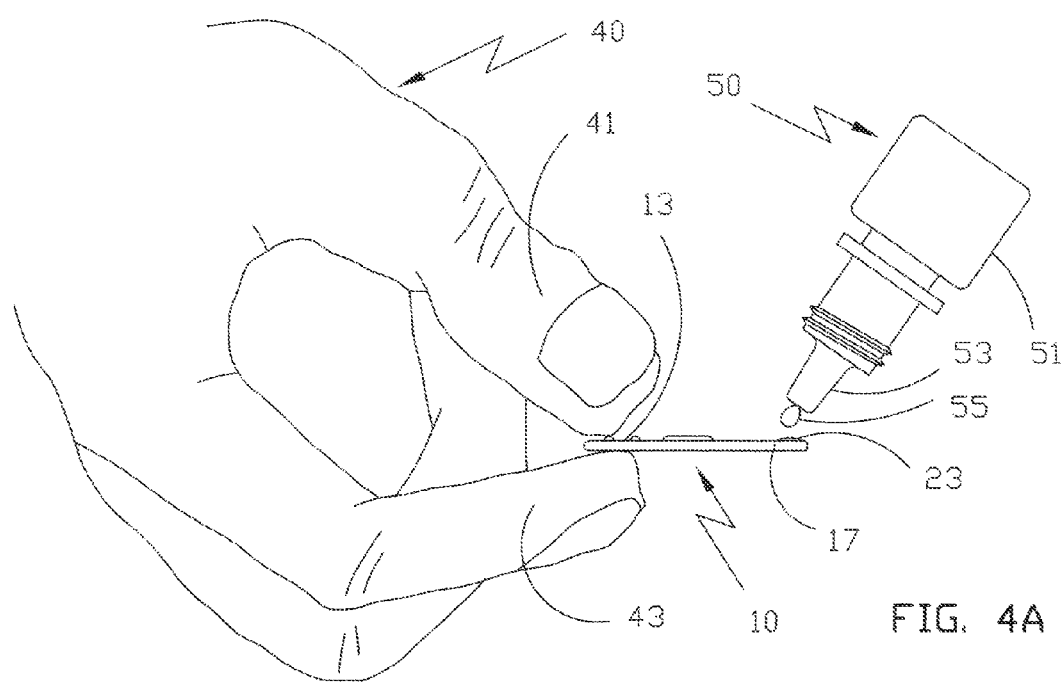
Figure 4B:
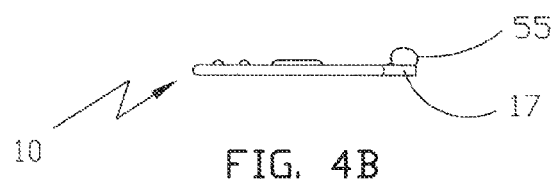

FIG. 4A illustrates a human hand 40 grasping the finger grip section 13 of the applicator 10 between a thumb 41 and forefinger 43. The other hand (not illustrated) grasps a dispenser bottle 50 containing eye drop solution and having a compressible body 51 and dispenser nozzle 53. Squeezing the bottle produces a drop 55 which is directed onto the dome 23 of the drop adhesion section 17 resulting in the adhered drop as illustrated in FIG. 4B.

Figure 4C:
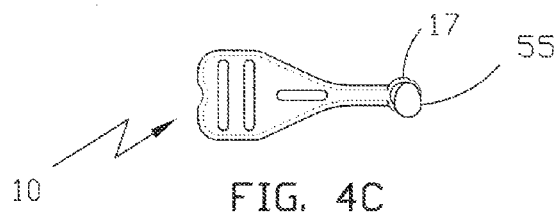
Figure 4D:

Preferably, the applicator 10 can be rotated without the drop falling off, by 90° as illustrated in FIG. 4C, still more preferably, by 180° as illustrated in FIG. 4D. Although not essential to have the degree of adhesion illustrated, the remaining steps are much easier if the degree of adhesion is as shown.

Figure 5A:
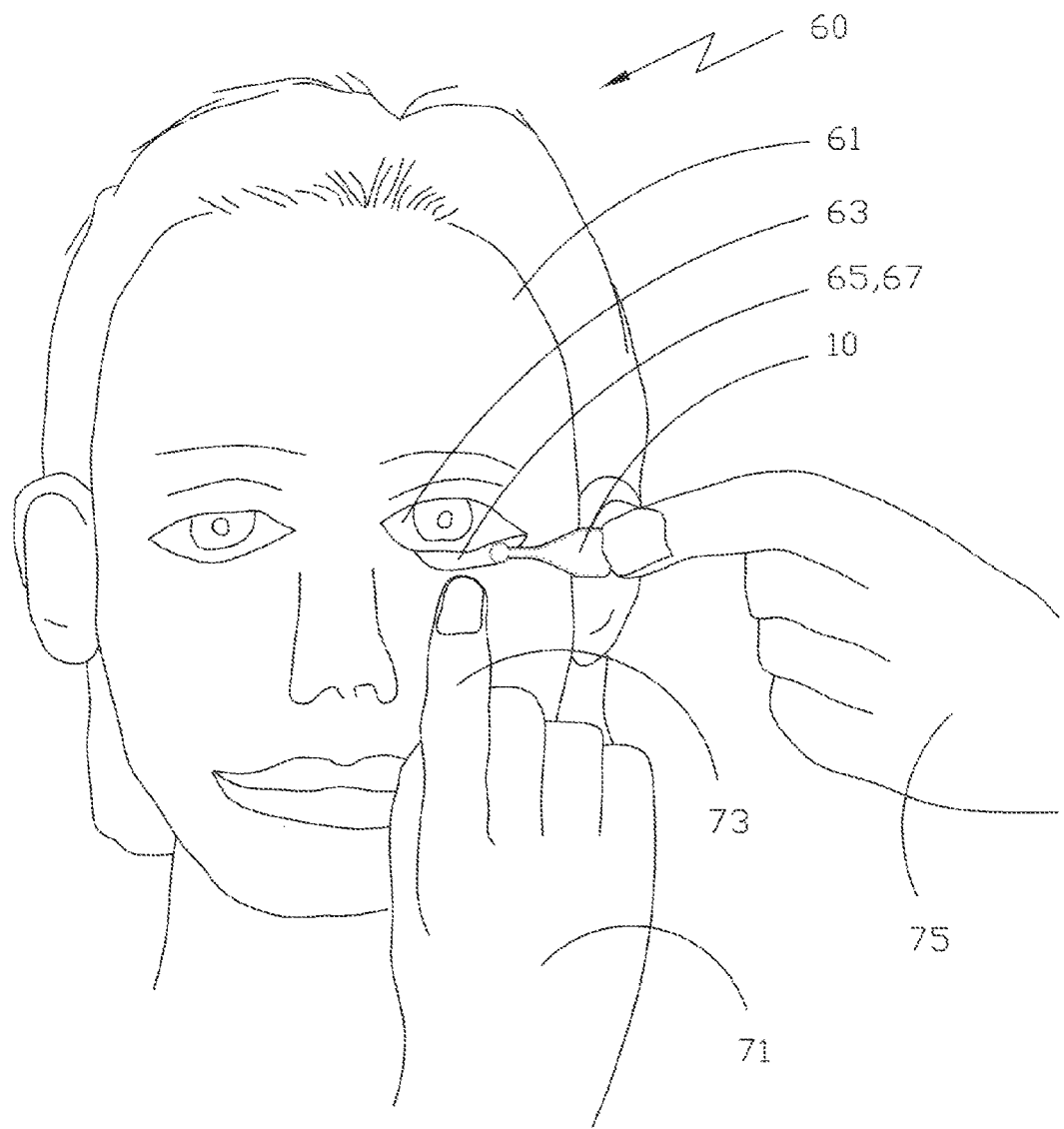

FIG. 5A illustrates a method of transferring the adhered drop 55 (not illustrated) into the (in this example) left eye 63 of a subject 60. Although not always essential (as explained further below), the subject 60 looks straight into a mirror (not illustrated) with an upright head 61. One hand 71 uses a finger 73 to gently pull down the lower eyelid 65 to expose the conjunctival sac 67 which acts as a trough for liquids. The other hand 75 holds the applicator 10 and brings it toward the eye from the side using peripheral vision. Unlike the typical eye drop dispenser method, it is not necessary to position anything directly in front of the eye so that a blink-response can be avoided. Keeping the plane of the applicator more or less vertical as illustrated, it should gently touch, ideally, the conjunctiva surface on the inside of the lower eyelid 65 with the adhered drop 55 (not illustrated) on the end of the applicator 10. However, the applicator is pliable enough that it may touch anywhere on the conjunctiva or even the cornea. After drop 55 (not illustrated) touches, substantially all of it transfers off the applicator.

Figure 5B:
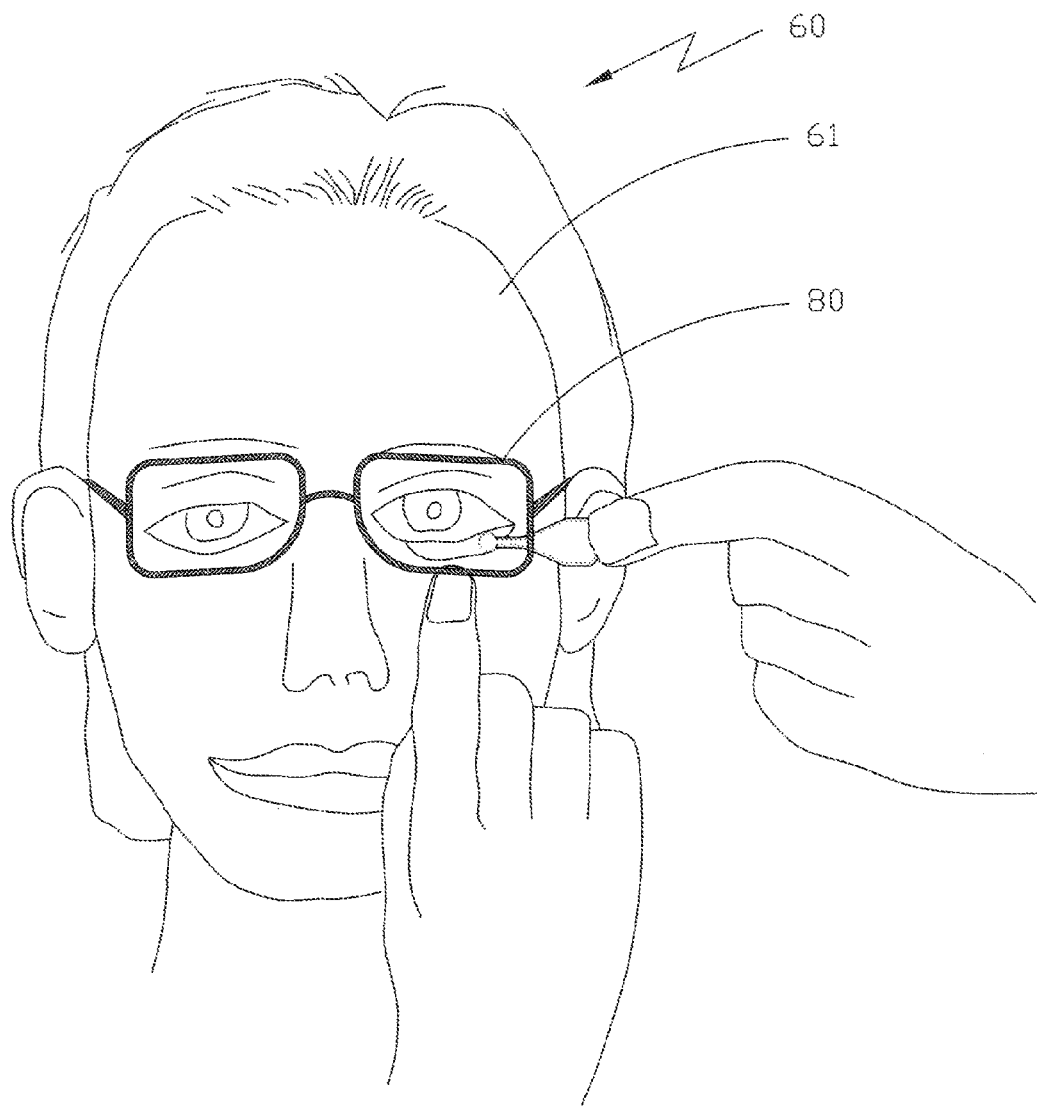

FIG. 5B illustrates the same method for a subject wearing eyeglasses 80 during the procedure. In most cases, it is not necessary to remove them. This makes it easier for some subjects to see what they are doing during the transfer process.

Informal In-House Trials:

Using prototype samples constructed according to FIGS. 1A-2B, in house trials were conducted. Two persons with experience with prior art eye drop applicators and the conventional method discussed in the Background section of tilting the head back and allowing drops to fall into the eye took part. Both testers normally wear corrective lenses. One could self-administer, but with difficulty because of a serious blink response. The other normally used a second person to hold, aim, and squeeze eye drop bottles while they held their top and bottom eyelids open with both hands.

Both testers found that it was straightforward to get a drop to adhere to the domed drop adhesion section 23, providing the drop was not too big. For reasonable sized drops, the applicator 10 could be slowly rotated 360° about its long axis without the drop falling off. This greatly facilitated use of the applicator since it was not necessary to keep the drop facing upward at all times.

Following the method illustrated in FIGS. 4A-5B (both wore glasses during the process), with the aid of a mirror but otherwise unaided, the testers reported being very comfortable getting drops into their eyes. Since the applicator came in from the side, there was no serious blink response. Transfer of a drop to the eye felt smooth with no sensation of poking the eye.

Regarding pliability, the extension section 15, see FIG. 1A, could easily be bent back almost flat onto the finger grip section 13. Based on these trials, lower durometer material might be too flexible to handle and apply drops to while higher durometers might be stiff enough to cause eye irritation if it is touched.

Drop Adhesion Structure Development:

The drop adhesion structure 23, illustrated in FIG. 1A and, more clearly, in FIG. 1B, was the culmination of experiments with initial LSR prototypes. These worked to a certain extent, but were judged not as effective as the version just mentioned. In that version, adhesion structure 23 can be characterized as a domed shape protruding from the surface of body 11 of applicator 10.

Figures 6A, 6B:
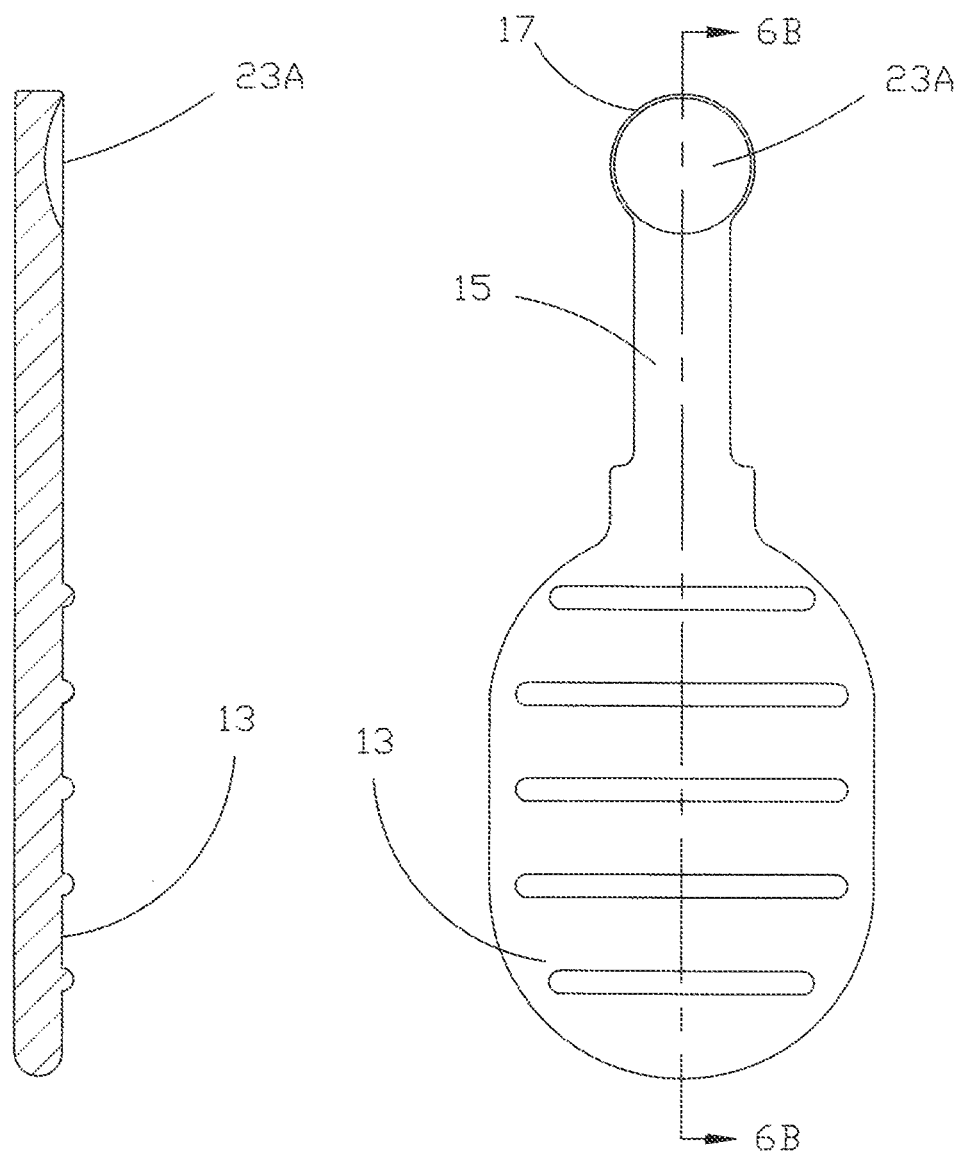

Initially, it was thought that a cup-shaped structure 23A, like a serving spoon, as illustrated in FIGS. 6A and 6B would work best. The thinking was that it would hold fluid applied from a dropper bottle. However, it was found that it held the liquid drop too well and did not allow for a smooth transfer into the end user eye. Additionally, residual liquid fluid was retained within the cup shape after transfer of the drop into the eye. Next, a variation with the cup replaced by a through-hole 23B, as illustrated in FIGS. 7A and 7B, was developed but liquid drop adhesion was too little.

A third variation, illustrated in FIGS. 8A and 8B, was produced with the fluid retention area 23C being simply flat. Drop adhesion was improved, but this shape was found not to retain a drop well when the applicator was rotated 360° about its longitudinal axis.

Figures 9A, 9B:
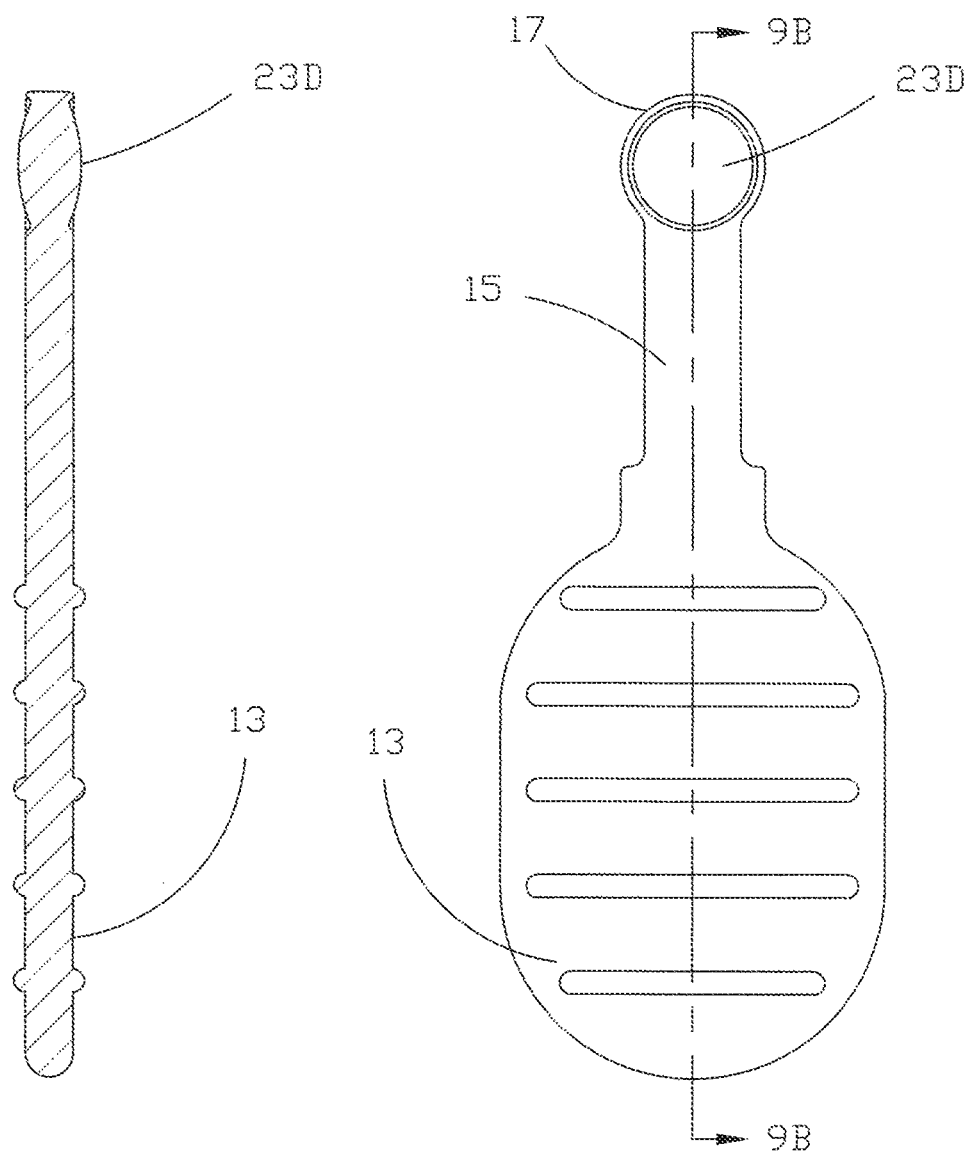

A fourth variation is illustrated in FIGS. 9A and 9B, with a drop adhesion structure 23D having a domed shape and a groove around the dome circumference. (The groove is hard to illustrate but it was about 0.026 in. (0.7 mm) wide and 0.006 in. (0.15 mm) deep compared to the dome height of 0.020 in. (0.5 mm). The results were improved adhesion but the groove retained fluid and impaired a smooth drop transfer into the eye. The resulting final variation was developed by removing the grooved ring around the drop adhesion structure 23 and changing the finger grip section 13 as illustrated in FIGS. 1A-1B.

Informal trials determined that this final shape, all produced with an LSR material, yielded the best results and met all the performance characteristics to transfer a liquid drop into the eye as described above.

Larger Drop Sizes:

Working examples described above were tested with the size of the drop determined by the device tip geometry. However, it was found that dispenser bottles dispense drops that are larger, up to two times, what the eye cul-de-sac can hold, typically given as 25 µL. Therefore, additional embodiments were constructed, optimized for use with a conservative 30 µL and even an excessive 50 µL drop. While this may be wasteful, it was judged a better option for the user to have excess medication run out of the eye than off the device.

For testing, four embodiments, discussed previously, and twenty two new embodiments were used. These all had the same basic structures illustrated in FIGS. 1A, 1B, 2A & 2B, but there were variations as described next with reference to FIGS. 10A-15D. In the figures, numerals 13, 15, and 17 are provided for a reference, but not referred to unless there is a difference from FIGS. 1A-2B. Note that, since a device can be made with different sides, each side is considered an embodiment for testing purposes. In commercial use, however, a device could be identical on both sides, inoperative on one side, or provide two different embodiments, one on each side.

Note also, that a number of embodiments are structurally identical, but differ in the plastic material used for manufacture which will be described separately.

Figures 10A, 10B:
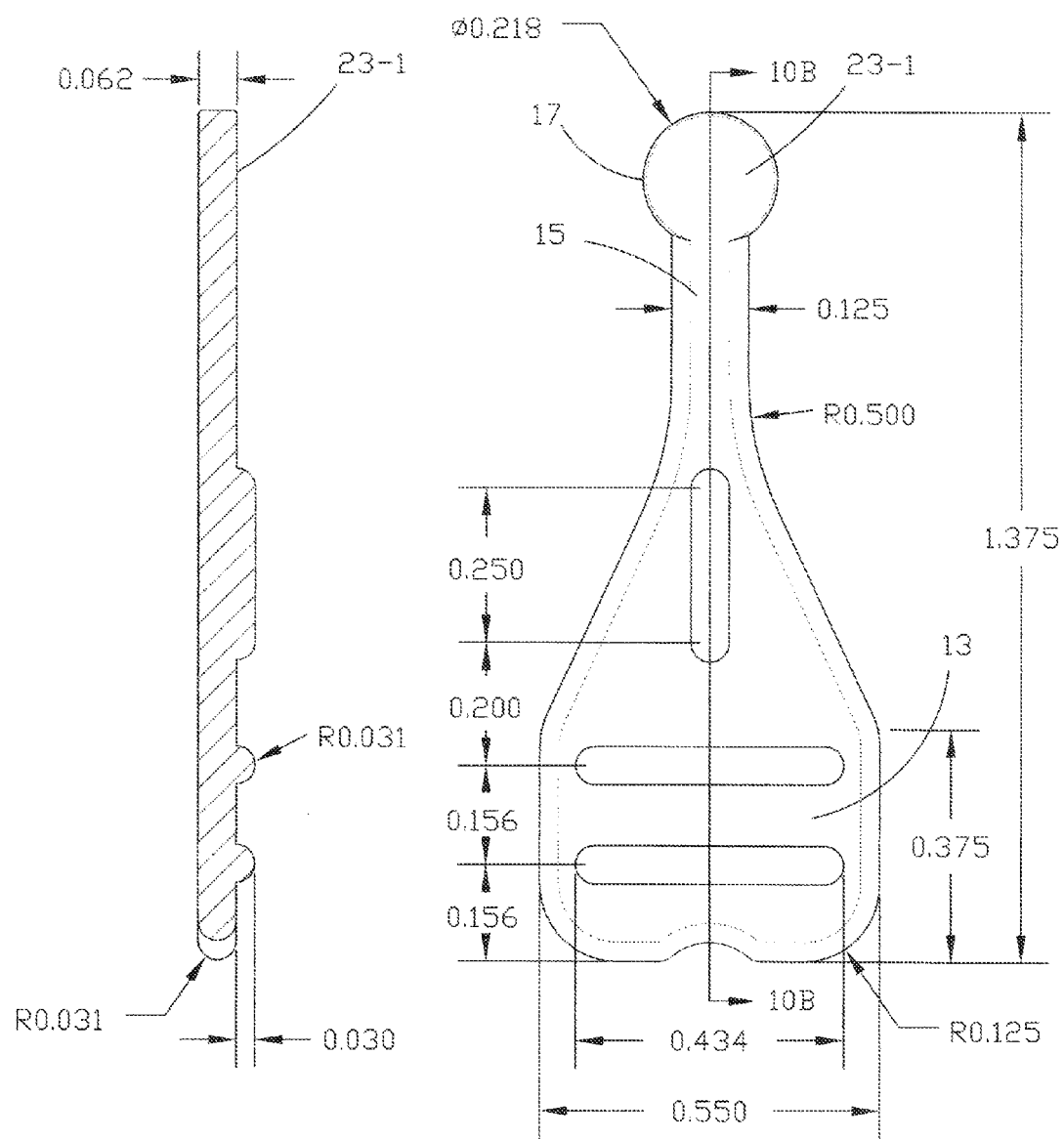

FIG. 10A is a top plan view of embodiment no. 1. It is dimensionally the same as FIG. 2A except that the drop adhesion structure 23-1 (23-XY indicates a drop adhesion section for embodiment no. XY which may be the same for more than one embodiment.) is flat, as shown in the cross-section, FIG. 10B.

Figure 11B:
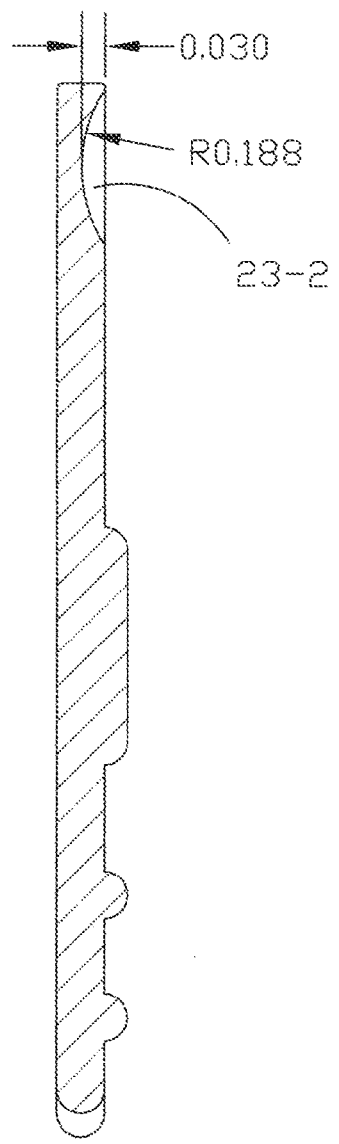
Figure 11A:
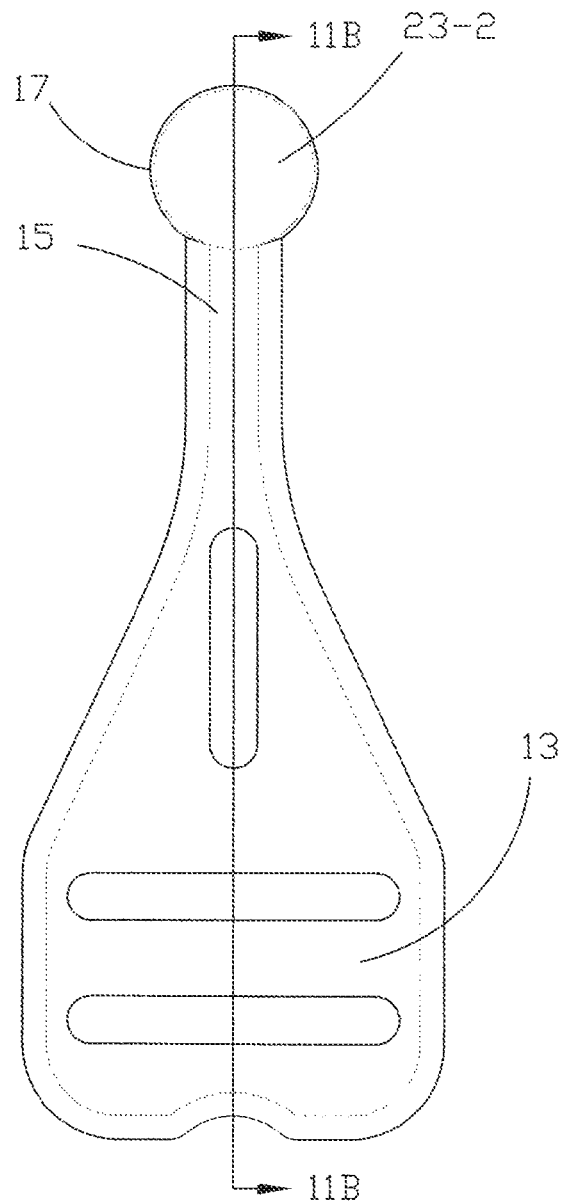

FIG. 11A is a top plan view of embodiment no. 2. It is dimensionally the same as FIG. 2A except that the drop adhesion structure 23-2 is a cup, as shown in the cross-section, FIG. 11B.

Figures 12A, 12B:
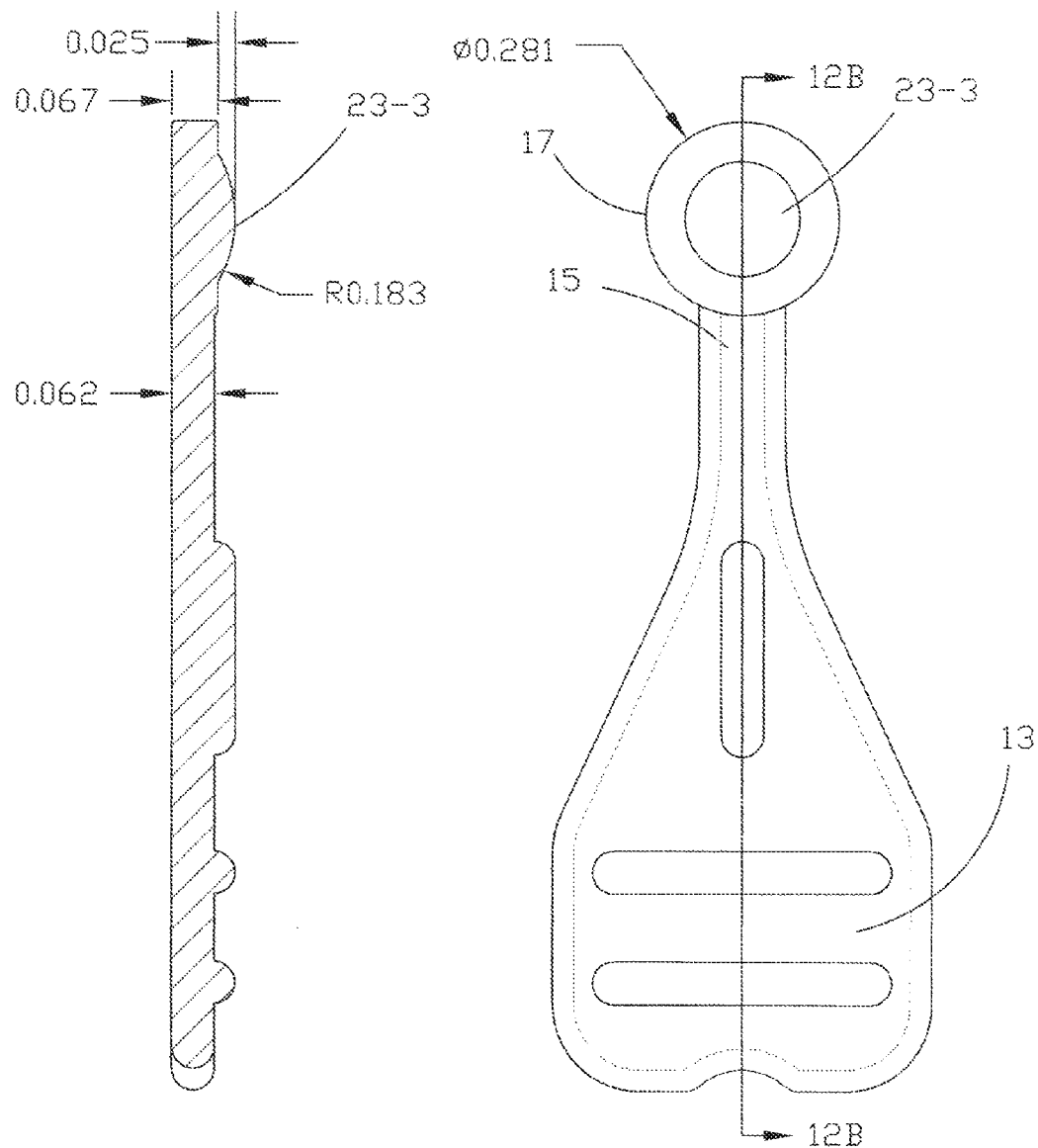
Figure 12D:
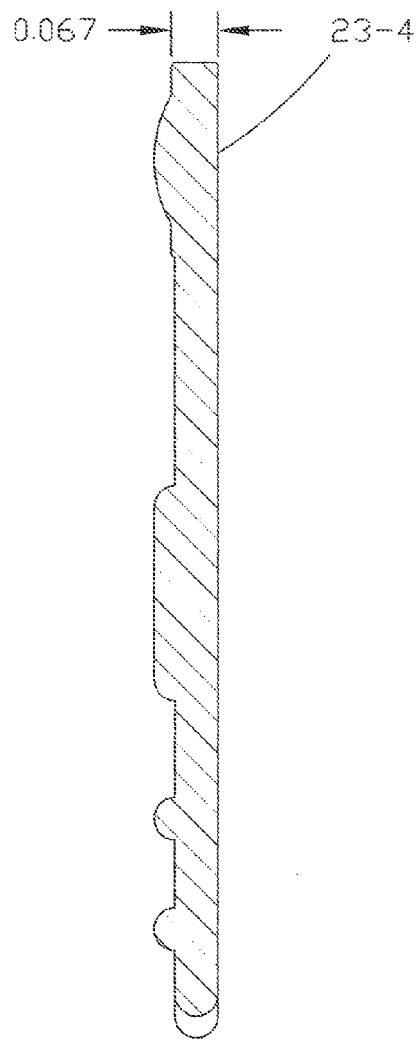

FIG. 12A is a top plan view of embodiment no. 3. It is dimensionally the same as FIG. 2A except that the outer diameter of the drop retainer portion 17 is now 0.281 in. (7.1 mm). As shown in the cross-section, FIG. 12B, the drop adhesion structure 23-3 comprises a spherical dome that is 0.025 in. (0.6 mm) high with a radius of 0.183 in. (4.6 mm).

Figure 12C:
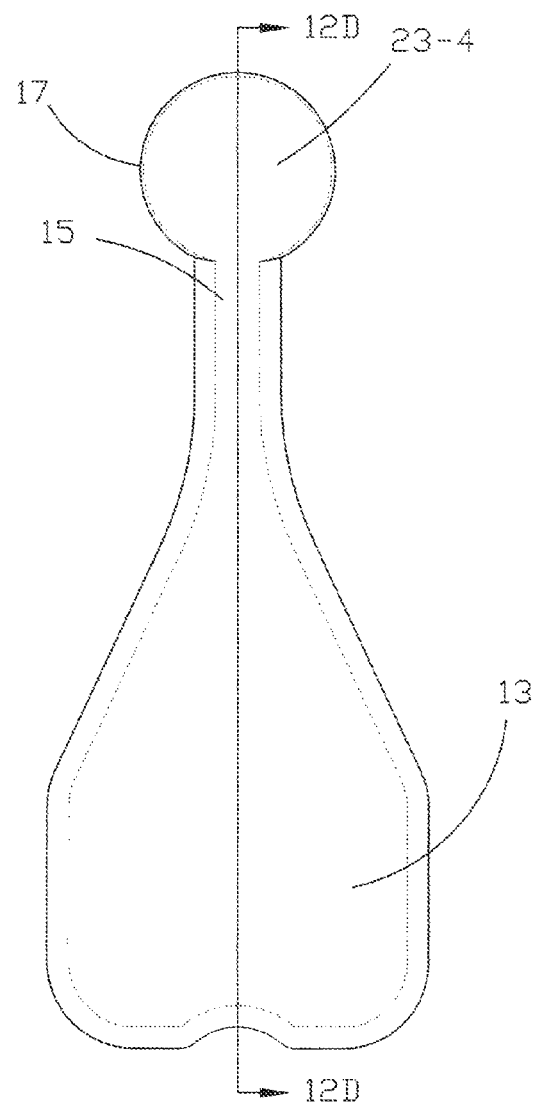

FIG. 12C is a top plan view of embodiment no. 4. It is actually the bottom of embodiment no. 3. In this case the drop adhesion structure 23-4 is flat, as shown in the cross-section, FIG. 12D.

Figures 13A, 13B:
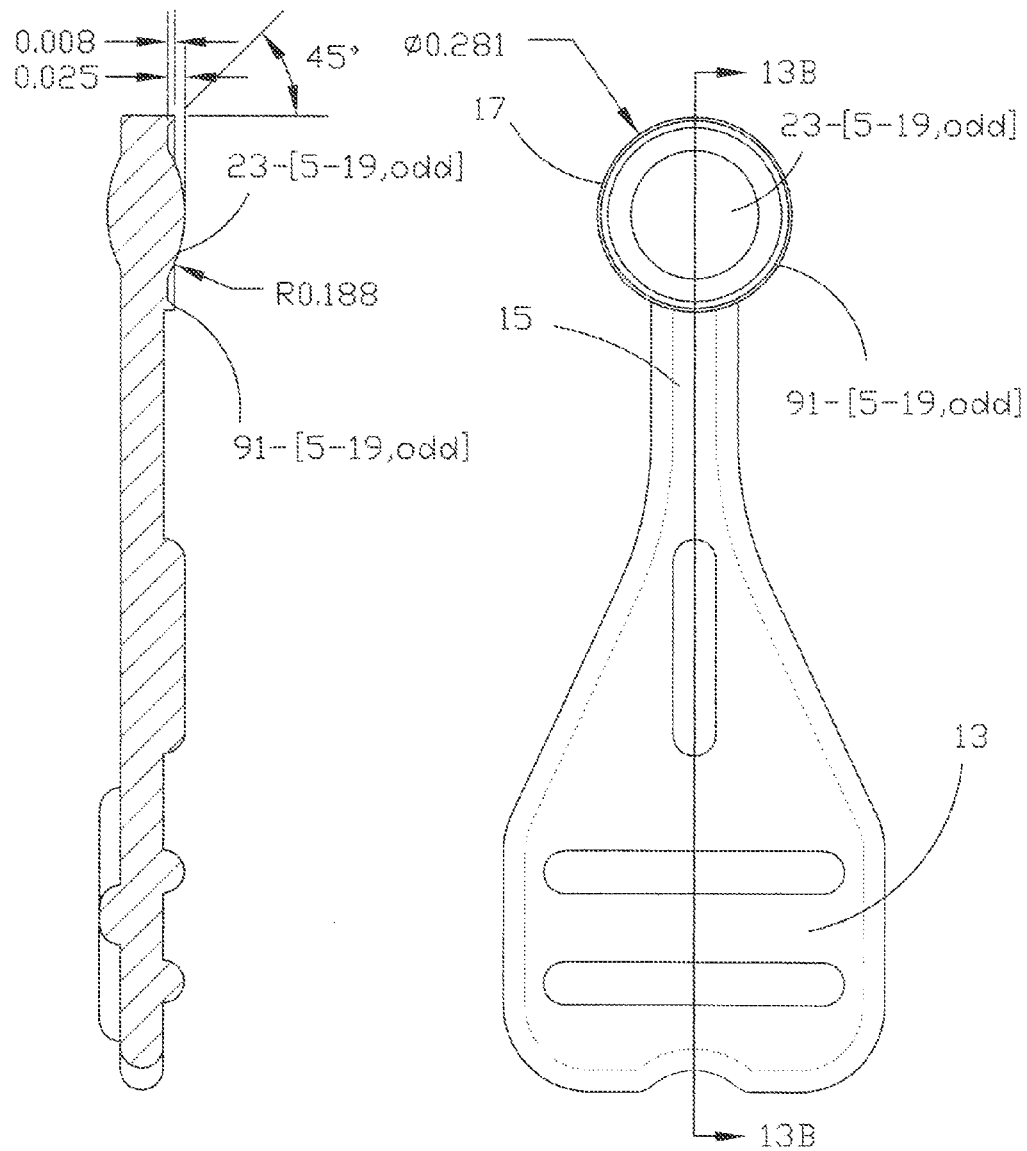

FIG. 13A is a top plan view of embodiment nos. 5-19, odd. As shown in cross-section FIG. 13B, for these embodiments, namely, 5, 7, 9, 11, 13, 15, 17, & 19, the drop adhesion structure 23-[5-19, odd] comprises a spherical dome, with a radius of 0.188 in. (4.8 mm) and a height of 0.025 in. (0.6 mm), surrounded by a ring 91-[5-19, odd] having a height of 0.008 in. (0.2 mm), sloping inward at a nominal 45°.

Figures 13C, 13D:
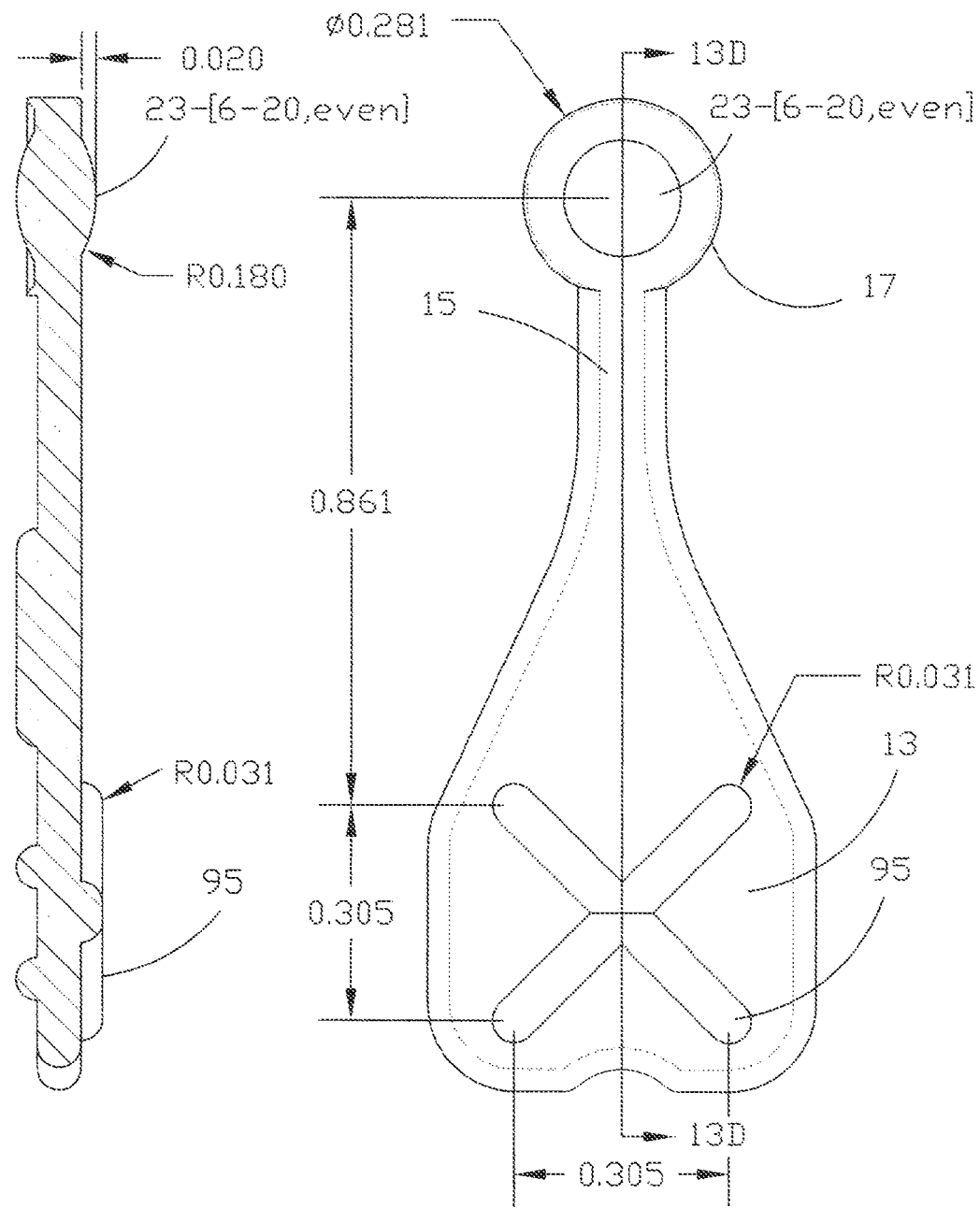

FIG. 13C is a top plan view of embodiment nos. 6-20, even, which are the other side of embodiments 5-19, odd, respectively. These differ from previous embodiments in that a cross 95 has been added to the finger grip portion 13. As shown in cross-section FIG. 13D, for these embodiments, namely, 6, 8, 10, 12, 14, 16, 18, & 20, the drop adhesion structure 23-[6-20, even] comprises a spherical dome, with a radius of 0.180 in. (4.6 mm) and a height of 0.020 in. (0.5 mm), not surrounded by a ring.

Figures 14A, 14B:
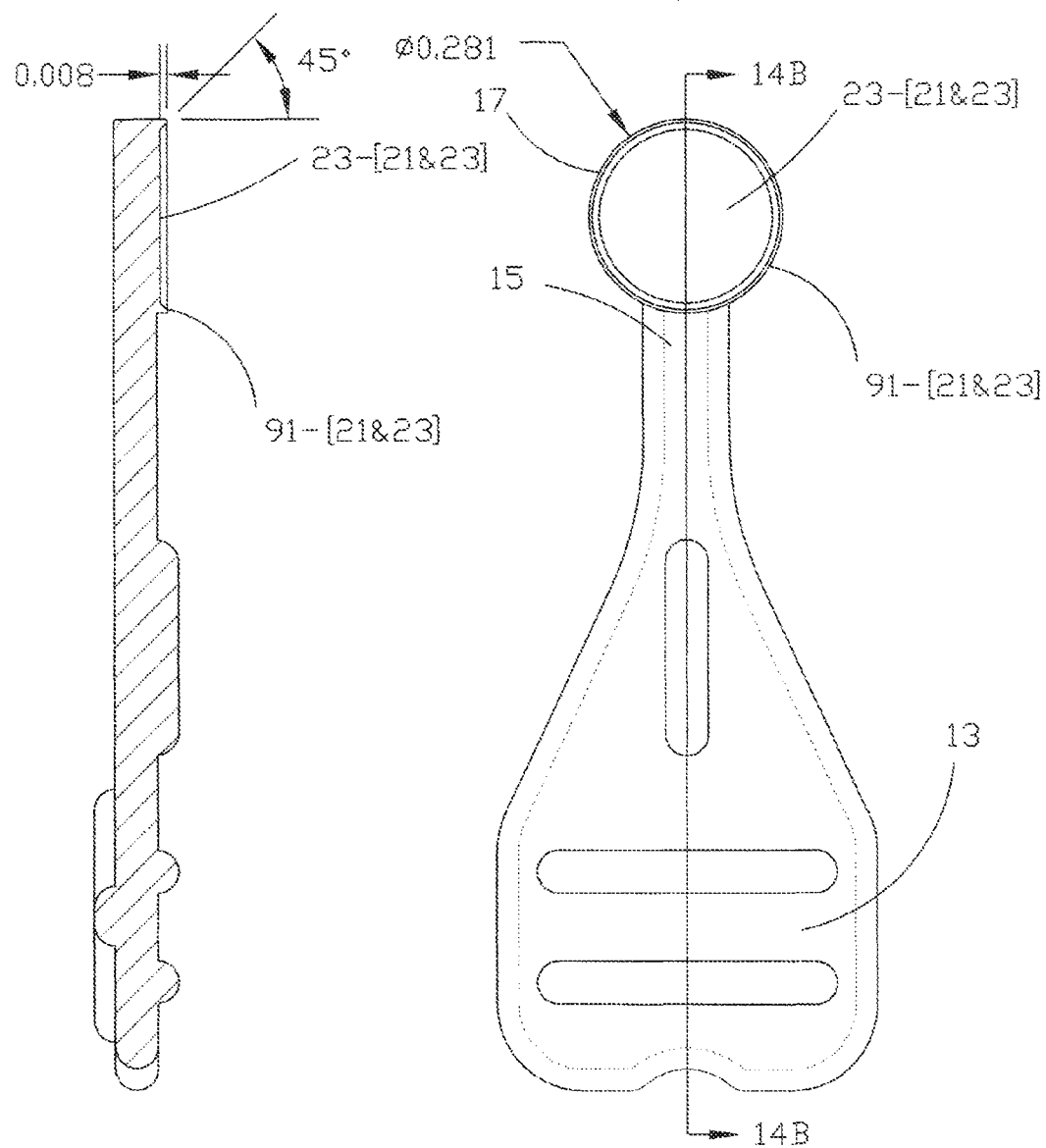

FIG. 14A is a top plan view of embodiment nos. 21 & 23. As shown in cross-section FIG. 14B, the drop adhesion structure 23-[21&23] comprises a ring only having a height of 0.008 in. (0.2 mm), sloping inward at a nominal 45°.

Figures 14C, 14D:
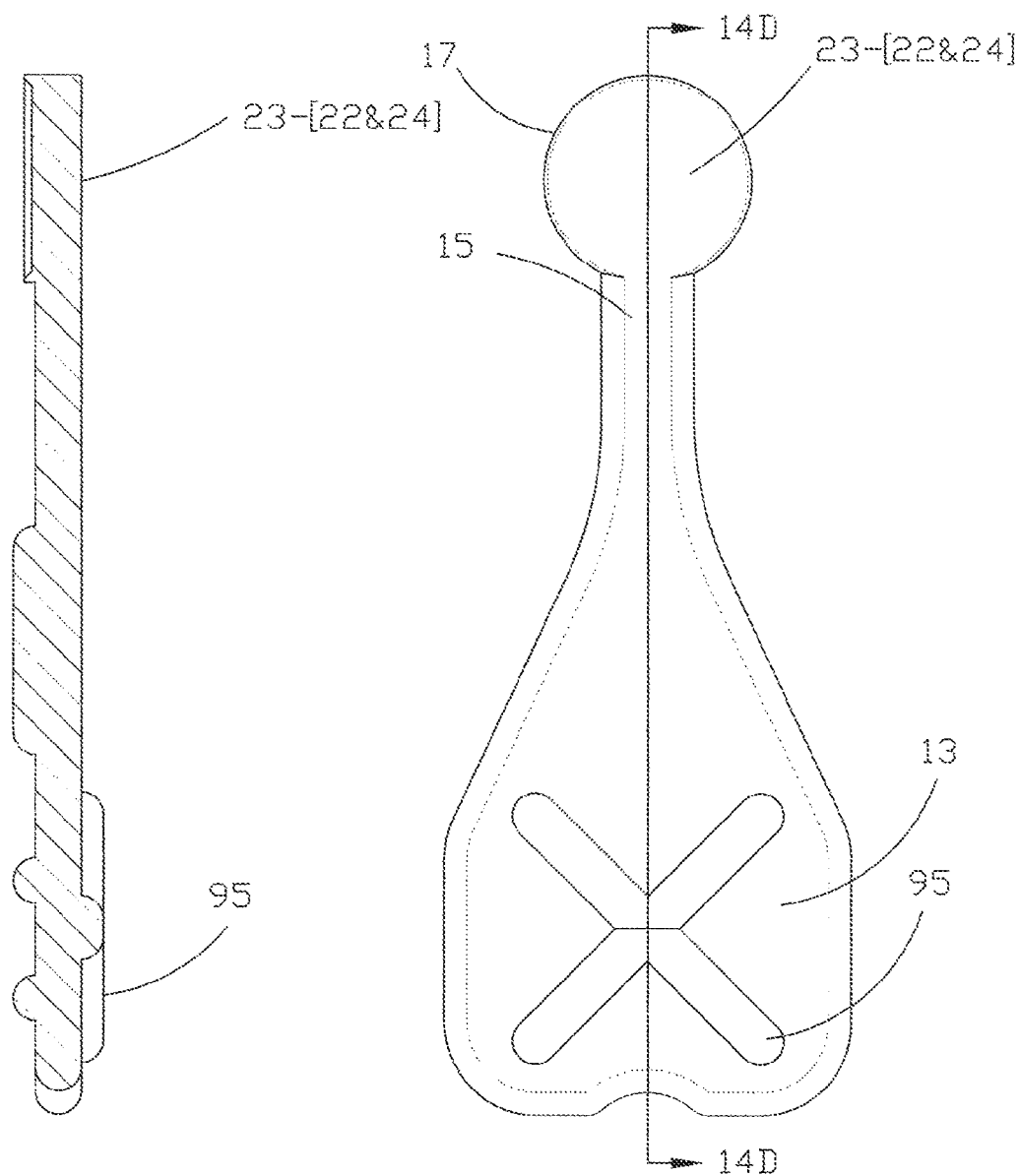

FIG. 14C is a top plan view of embodiment nos. 22 & 24, which are the other side of embodiments nos. 21 and 23, respectively. As shown in FIG. 14D, for these embodiments, the drop adhesion structure 23-[22&24] is flat.

Figures 15A, 15B:
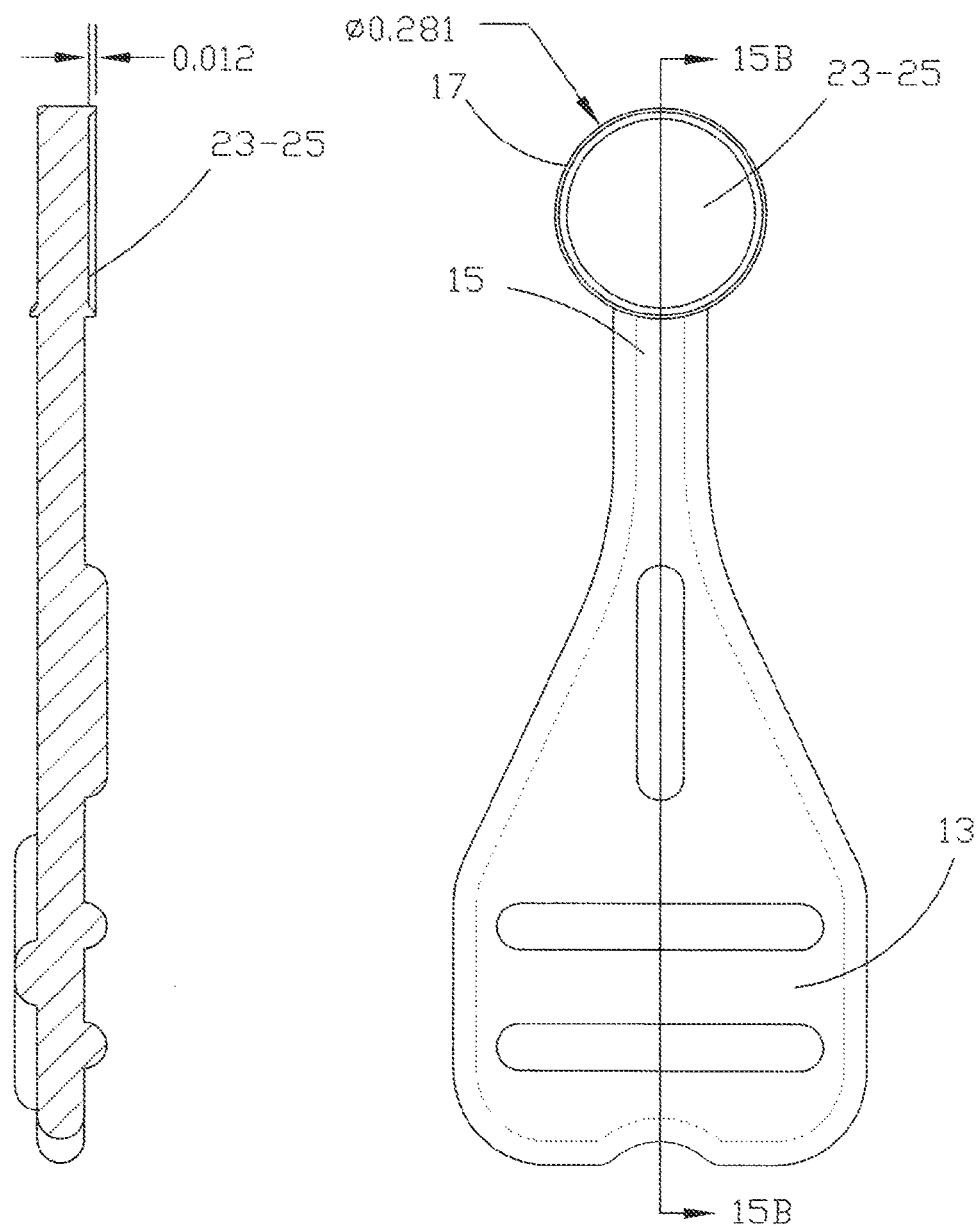

FIG. 15A is a top plan view of embodiment no. 25. As shown in cross-section FIG. 15B, the drop adhesion structure 23-25 comprises a ring only, but having a height of 0.012 in. (0.3 mm), sloping inward at a nominal 45°.

Figures 15C, 15D:
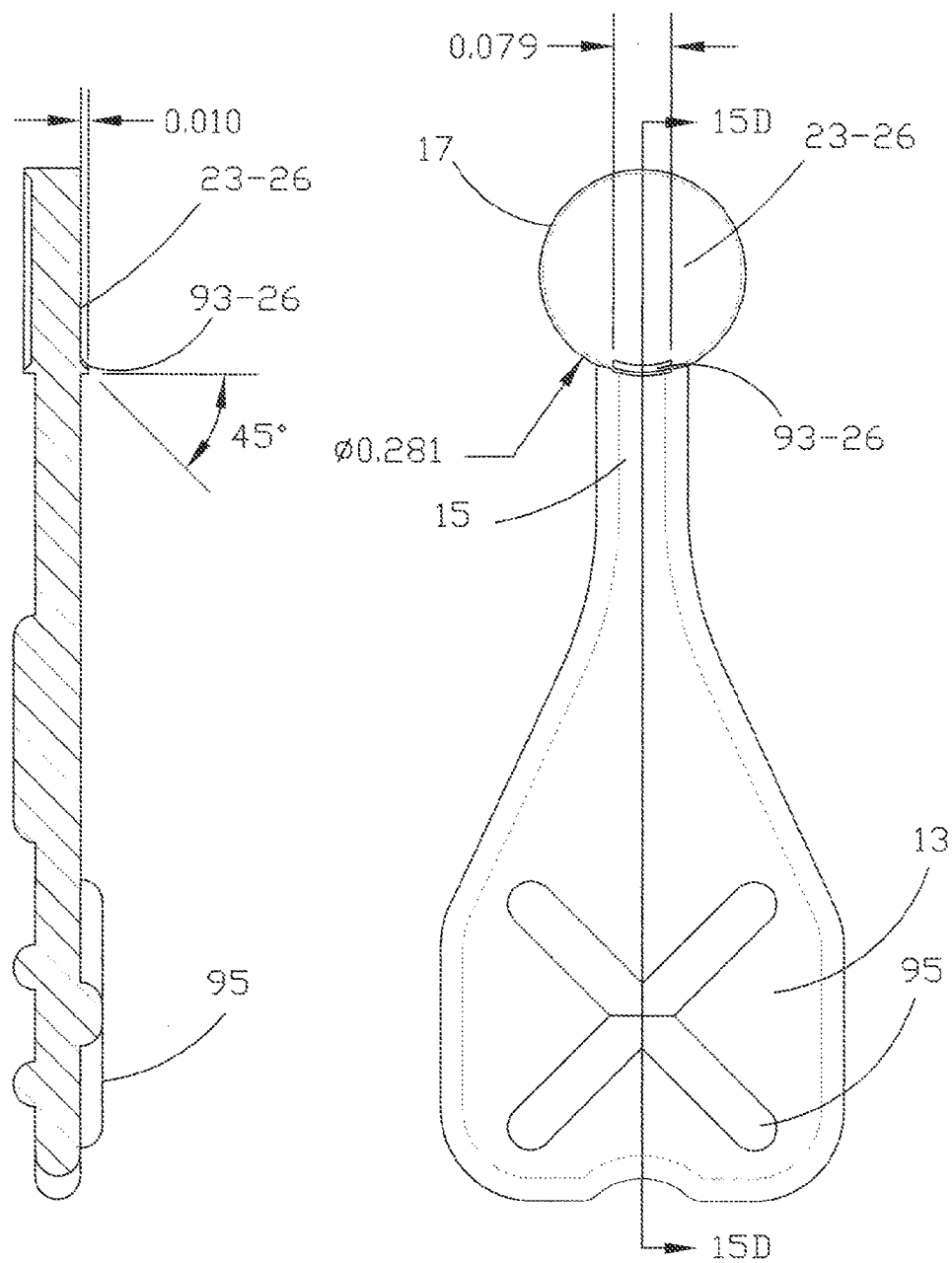

FIG. 15C is a top plan view of embodiment no. 26, which is the other side of embodiment no. 25. This differs from other embodiments in that there is a partial circular dam 93-26 between it and the extension 11. As shown in cross-section FIG. 15D, for this embodiment, the drop adhesion structure 23-26 is flat. The partial circular dam 93-26 has a height of 0.010 in. (0.25 mm) and slopes inward at a nominal 45°.

Plastic Materials:

Although LSR is well accepted for use in medical devices, it was found that drop retention was aided by its tendency to collect particles (lint) when cleaned with a dry cloth. Since a clean surface is required for sterility, other materials were investigated. These were all different formulations of thermoplastic elastomers (TPE) as opposed to LSR which is a thermoset. As a general rule, TPEs are less costly in terms of materials and processing than thermosets. Several of these were tried with varying degrees of success.

Various brands were tried:

a) The first one was Santoprene™ 8211-35, a trademark of Exxon Mobile. This is a non-hygroscopic thermoplastic vulcanizate in the thermoplastic elastomer (TPE) family. A formulation with a cured hardness of 40 Shore A was used.

b) The second was Vistamaxx™ 6102, also a trademark of Exxon Mobile. This is a propylene-based olefinic TPE. A formulation with a cured hardness of 66 Shore A was used.

c) The third was C-Flex®, a trademark of Compagnie de Saint-Gobain. A formulation with a cured hardness of 40 Shore A was used.

d) The fourth was Enflex S4065A Natural, supplied by Emplast Polymers, LLC of Orlando, Fla. This is a styrenic block copolymer based TPE. A formulation with a cured hardness of 65 Shore A was used.

e) The fifth one, the last one tried was Hytrel® 3078, a trademark of DuPont. This is a thermoplastic polyester elastomer. A formulation with a cured hardness of 30 Shore D was used. To enhance the contrast between a typical water clear color eye drop and the device surface, a color concentrate, PolyOne #CC10176235WE NV BLUE was added to the Hytrel material used for embodiment nos. 21-26. It was not believed that any mechanical properties would be affected by the color additive. However, after test 6 (below), it was found that after 3 weeks of accelerated aging simulating 12 months at room temperature, drop adhesion was substantially impaired unless the surface was washed prior to use. The same did not occur for Hytrel samples made without added colorant.

Except for Enflex, suppliers of the other plastic formulations are world renowned and easily located by searching the Internet with the trade names.

Drugs Used:

Several types of prescription eye drops were used during the development of the device. The drug selection included varying applications for, glaucoma, ocular hypertension, inflammation, allergic conjunctivitis, and ocular pain. One over-the counter lubricating eye drop was used for the typical application at the users discretion for temporary relief of general discomfort. The following is a brief thumbnail description of the drugs used, listed by brand name.

a) Alrex®, a trademark of Bausch & Lomb, Inc., is a prescription only loteprednol etabonate ophthalmic suspension for use as a topical anti-inflammatory corticosteroid.

b) Alphagan® P, a trademark of Allergan, Inc., is a prescription only alpha adrenergic receptor agonist used for patients with glaucoma or ocular hypertension.
c) Azopt®, a trademark of Novartis AG Corp., is a prescription only carbonic anhydrase inhibitor used for patients with glaucoma or ocular hypertension.
d) Bromday®, a trademark of ISTA Pharmaceuticals, Inc., is a nonsteroidal anti-inflammatory drug used for the treatment of postoperative inflammation and reduction of ocular pain in patients who have undergone cataract extraction.
e) Durezol, a trademark of Novartis AG Corp., is a prescription only topical corticosteroid that is used for the treatment of inflammation and pain associated with ocular surgery.
f) Lastacaft™, a trademark of Allergan, Inc., is a prescription only histamine receptor antagonist used for the prevention of itching associated with allergic conjunctivitis.
g) Nevanac®, a trademark of Novartis AG Corp., is a prescription only nonsteroidal anti-inflammatory prodrug used for the treatment of pain and inflammation associated with cataract surgery.
h) Blink Tears™, a trademark of Abbott Medical Optics, Inc., is an over-the-counter lubricating eye drop used for the temporary relief of burning, irritation, and discomfort due to dryness of the eye or exposure to wind or sun.

In the following, for ease of presentation, trademarks will be used without superscripts with the understanding that it is not in derogation of trademark owners' rights in the marks.

Working Embodiments for Testing

The invention took the form of various embodiments characterized by different materials and geometries. A total of 26 were manufactured. As will become clearer below, most embodiments (5-26) represent one side or the other of a single piece. As discussed previously, eye drops are dispensed with different volumes depending on the use and cost. The cul-de-sac of an eye can hold at most 25 µL of fluid. Expensive glaucoma and other prescription medicine bottles typically dispense this approximate volume, so 30 µL was used for the testing described next. Over-the-counter eye lubricants are much less expensive and the bottles dispense an apparently excessive amount, typically, 50 µL. As a result, one side of each dispenser, named herein the Rx side, was usually directed to the smaller volume. The other side, named herein the OTC side, was directed to the larger volume. The designation is based on the increased difficulty of holding a 50 µL drop. Of course, there is nothing that requires that a device is made to optimize both drop sizes. However, it was convenient at this stage to make two different sides on each sample.

Below, Table 1 lists each embodiment, identifying the material, a side (RX or OTC if appropriate), the figure number for the tip design, a short description, the height of a ring, if any, and other characteristics, if any. Other than LSR, materials are specified by trade name. The diameter of the tip was 0.281 (7.1 mm) unless noted. LSR embodiments 11 & 12 were coated with parylene to reduce attraction of lint, but these were the only ones. Polished embodiments had an SPI A-2 finish and textured ones had an SPI D-1 finish.

Not all embodiments were used in each experiments described in the next section and the embodiments evolved based on feedback from experiments and availability of materials. However, a complete listing at the outset may serve as a roadmap for the reader to the optimum solution. (Metric equivalents were given above.)

TABLE 1

Listing of Working Embodiments

| Emb. | Material | OTC/Rx | FIGS. | Description | Ring height, if any | Other, if any 0.281 dia. tip, unless noted |
|---|---|---|---|---|---|---|
| 1 | LSR | n/a | 10A,B | Flat | | 0.218 dia. tip |
| 2 | LSR | n/a | 11A,B | Cup | | 0.218 dia. tip |
| 3 | LSR | n/a | 12A,B | Dome | | |
| 4 | LSR | n/a | 12C,D | Flat | | |
| 5 | Santoprene | OTC | 13A,B | Dome | 0.008 | |
| 6 | Santoprene | Rx | 13C,D | " | | |
| 7 | Vistamaxx | OTC | 13A,B | " | 0.008 | |
| 8 | Vistamaxx | Rx | 13C,D | " | | |
| 9 | C-Flex | OTC | 13A,B | " | 0.008 | |
| 10 | C-Flex | Rx | 13C,D | " | | |
| 11 | LSR-Parylene | OTC | 13A,B | " | 0.008 | |
| 12 | LSR-Parylene | Rx | 13C,D | " | | |
| 13 | Enflex | OTC | 13A,B | " | 0.008 | |
| 14 | Enflex | Rx | 13C,D | " | | |
| 15 | Hytrel | OTC | 13A,B | " | 0.008 | |
| 16 | Hytrel | Rx | 13C,D | " | | |
| 17 | Hytrel | OTC | 13A,B | " | 0.008 | |
| 18 | Hytrel | Rx | 13C,D | " | | |
| 19 | Hytrel | OTC | 13A,B | " | 0.008 | |
| 20 | Hytrel | Rx | 13C,D | " | | |
| 21 | Hytrel | OTC | 14A,B | Flat | 0.008 | |
| 22 | Hytrel | Rx | 14C,D | " | | Textured |
| 23 | Hytrel | OTC | 14A,B | " | 0.008 | |
| 24 | Hytrel | Rx | 14C,D | " | | Polished |
| 25 | Hytrel | OTC | 15A,B | " | 0.012 | |

TABLE 1-continued

Listing of Working Embodiments

| Emb. | Material | OTC/Rx | FIGS. | Description | Ring height, if any | Other, if any 0.281 dia. tip, unless noted |
|------|----------|--------|-------|-------------|---------------------|-------------------------------------------|
| 26   | Hytrel   | Rx     | 15C,D | "           | 0.010 Dam Section   | Polished                                  |

Test Results:

A number of experiments were conducted on various embodiments. Some results are based on subjective look and feel, while others are based on more precise measurements. The major goal was to improve on the initial LSR embodiments for the larger 50 µL drop sizes dispensed by OTC eye lubricants. This improves some, but not necessarily all aspects, of the smaller 30 µL drop size prescription medication.

Not all embodiments were involved and not all fluids were used in every test. Blink Tears was used as the default liquid drop because it was available OTC. Tests are discussed substantially in the date order performed. In hindsight, different tests in a different order might appear to have been more efficient but, serendipitously, the end result was successful.

As a preliminary on adhesion time, in use as discussed previously, a patient transfers a drop to the device while it is horizontal, turns it 90°, and applies the drop to the eye. Obviously, it is important that the drop adheres to the device during this process. To quantify adhesion a bit, a sturdy precision jig was used to measure adhesion time in seconds. The jig was adapted to hold a device and rotate it 90° via a one-to-one hand crank. To simulate use, the cranking speed was such as to rotate 90° in about one second, using an electronic timer. As used herein, "adhesion time" is the time the drop stayed on the device after rotation by 90°. An adhesion time of zero means the drop fell off before 90° of rotation was accomplished.

Another important attribute of the device was the amount of the initial drop transferred. In other words, since the goal is to transfer fluid to the eye, there is such a thing as too much adhesion. This was measured both subjectively and using a precision gram scale. Fluid drop size was measured by volume using a Gilson metered fluid dispenser.

Test 1. Drop Adhesion versus Tip Shape: The adhesion time and drop retention were measured for some embodiments having two different basic tip shapes, either with a dome or flat. The same device had two sides, denominated above as Rx and OTC, but a different embodiment number is assigned to each side. A complete description was given above for each embodiment, but salient characteristics are in the table below. Blink Tears was used for all tests with 50 µL and 30 µL drop sizes.

Adhesion time was recorded up to 15 seconds. Normally, this is far longer than is needed to use the device, but is a rough indication of the degree of adhesion. Residue (visual % wetting) was determined approximately after a simulated transfer to a damp paper towel. Some combinations were repeated. Results appear in Table 2.

TABLE 2

Tip Shape Adhesion Comparison & Surface Coverage Residue

| Emb. | Material | Rx/OTC | Dome/Flat | Other    | Drop Size (µL) | Adhesion Time (sec) | Residue (%) |
|------|----------|--------|-----------|----------|----------------|---------------------|-------------|
| 17   | Hytrel   | OTC    | Dome      | Ring     | 50             | 15+                 | 75          |
| 17   | "        | "      | "         | "        | "              | 15+                 | 75          |
| 21   | "        | "      | Flat      | "        | "              | 15+                 | 40          |
| 21   | "        | "      | "         | "        | "              | 15+                 | 60          |
| 18   | "        | Rx     | Dome      |          | "              | 0                   | 50          |
| 18   | "        | "      | "         |          | "              | 0                   | 60          |
| 22   | "        | "      | Flat      | Textured | "              | 9                   | 50          |
| 22   | "        | "      | "         | "        | "              | 0                   | 50          |
| 18   | "        | "      | Dome      |          | 30             | 15+                 | 100         |
| 22   | "        | "      | Flat      | Textured | "              | 15+                 | 75          |

This test determined that the better tip shape was a flat geometrical shape and provided data to modify the design and continue development improvements.

Test 2. Liquid Drop Residue Test: A more precise measure of residue was made on embodiment no. 21 using a gram scale with a precision of 1 mg. After drop application, the device was rotated 90°. Most of the drop fell off, but the remainder was transferred to a damp towel. (If a drop falls off into the eye, this is not bad but here the aim was to find how little residue is left.) Device weight was measured before, after drop application, and after transfer using 50 µL of Blink Tears. From an average of seven trials, the dry weight was 559 mg, weight with a drop was 636+/−5 mg, and the weight after transfer was 564+/−4 mg. Thus, average drop weight was 77 mg and the residue was 4 mg, about 5.0%.

Another trial with a 30 µL drop of Blink Tears, which stayed on the device, produced a residue of about 6%. Still another with a 30 µL drop of the ophthalmic medication, Lastacaft, produced a residue of 11%.

Test 3. Tip Size and Surface Finish Test: Since the device is making a transfer directly to the eye, it would be desirable that it not be too large. However, it was found that drops applied to the device take up a surface area depending on device material and surface finish. Three different diameter discs were punched out of a flat piece of molded Hytrel. The Hytrel was molded with, qualitatively, both polished (SPI A-2) and textured (SPI D-1) mold surfaces. Trials were performed by depositing various size drops of Blink Tears on a horizontal disc, then rotating 90° and observing whether the drop stayed on or not for more than about one second with a yes/no result. Results appear in Table 3 for 0.250 in. (6.4 mm), 0.312 in. (7.9 mm), and 0.375 in. (9.5 mm) diameters.

TABLE 3

Tip Size & Surface Texture Adhesion

| Drop Size (μL) | 0.250 in. Polished | 0.250 in. Textured | 0.312 in. Polished | 0.312 in. Textured | 0.375 in. Polished | 0.375 in. Textured |
|---|---|---|---|---|---|---|
| 50 | No | No | No | No | No | No |
| 40 | No | No | No | Yes | No | Yes |
| 35 | No | No | No | Yes | No | Yes |
| 30 | Yes | Yes | Yes | Yes | Yes | Yes |

Larger drops fare better on larger diameters. Unfortunately, these are inconvenient for application to an eye. One can also see that textured surfaces are better than polished ones. Even for a textured surface, if the diameter is too small, large drops won't adhere. It looked like the 50 μL drops spread to 0.281 in. (7.1 mm)—halfway between 0.250 (6.4 mm) and 0.312 (9.5 mm). To make it possible to use the device for OTC solutions as well as Rx ones, 0.281 in. (7.1 mm) was chosen as a compromise.

Test 4A. Adhesion versus Ophthalmic Medicine Liquid—Textured Surface: For present purposes, the liquid properties of ophthalmic medicines are unknown. To test suitability for different medicines, embodiment no. 22, a Hytrel flat Rx side with no ring and a textured SPI D-1 finish was used. 30 μL of each medicine was applied to a horizontal device, which was turned 90° and the adhesion time measure. The same device was used, but washed and dried between each trial. The results of several trials for each drug appear in Table 4A:

TABLE 4A

Rx Eye Drop Adhesion

| Medicament | Adhesion Time (sec) |
|---|---|
| Alphagan | 60+ |
| Alrex | 60+ |
| Azopt | 60+ |
| Bromday | 0 |
| Durezol | 60+ |
| LastaCaft | 60+ |
| Nevanac | 3-11 |

Two of the medications adhered very poorly. Neither Bromday nor Nevanac are used to treat glaucoma, but are anti-inflammatories used in conjunction with cataract surgery. It was observed that the liquid had a very low viscosity which may be due to a different liquid carrier than the others.

Test 4B. Adhesion versus Ophthalmic Medicine Liquid—Polished Surface: To see if a polished surface would improve adhesion time for Bromday and Nevanac, embodiment no. 24, a Hytrel, flat Rx side with no ring was tested in the same way as in Test 4A. Results appear in Table 4B.

TABLE 4B

Rx Eye Drop Adhesion-Polished

| Medicament | Adhesion Time (sec) |
|---|---|
| Alphagan | 60+ |
| Alrex | 60+ |
| Azopt | 60+ |
| Bromday | 16 |
| Durezol | 60+ |

TABLE 4B-continued

Rx Eye Drop Adhesion-Polished

| Medicament | Adhesion Time (sec) |
|---|---|
| LastaCaft | 60+ |
| Nevanac | 20 |

Surprisingly, with a polished as opposed to a textured finish, Bromday improved from zero to 16 seconds and Nevanac from 3-11 to 20 seconds, while the others remained at 60+ seconds.

Bromday and Nevanac were also tested using embodiment no. 23, a Hytrel, flat OTC side with a 0.008 (0.2 mm) ring. The results were the same as Test 3 (worse than here), indicating that a polished finish is preferred for these two medicaments, irrespective of different geometries.

Test 5: Overall Performance Characteristics versus Material: There are several performance characteristics with varying degrees of importance. To obtain a general evaluation of different materials, three were tested for a number of them with an OTC eye drop, Blink Tears, and an ophthalmic medicine, Lastacaft. A 30 μL drop size was used for all tests. Three different materials were evaluated, LSR, Enflex, and Hytrel. The embodiment for LSR was nos. 11 and 12, for Enflex nos. 13 & 14, and for Hytrel nos. 17 & 18.

Subjective evaluations were undertaken by the inventor of adhesion, drop transfer, residue, shape memory (the ability to recover after bending double), finger feel of the finger grip portion, tear strength, and color contrast with drops. (All materials were natural color without color additives.) The evaluation of the non-liquid dependent characteristics, where the entire device was tested as a unit, was based on his long experience with producing similar products for other applications. Evaluation of the drop dependent characteristics was based on more recent experience. Drops of 30 μL were used for both the Rx and OTC side.

The results appear in Table 5. The scale is from 1=poor, 2=marginal, 3=fair, 4=good, and 5=excellent.

TABLE 5

Material Performance Tests:

| Characteristic\Emb.: | Enflex nos. 13 & 14 | | LSR nos. 11 & 12 | | Hytrel nos. 17 & 18 | |
|---|---|---|---|---|---|---|
| Medicine: | Blink | LastaCaft | Blink | LastaCaft | Blink | LastaCaft |
| Rx Side | | | | | | |
| Adhesion | 1 | 1 | 2 | 2 | 3 | 3 |
| Transfer | 1 | 1 | 2 | 2 | 2 | 2 |
| Retention | 4 | 4 | 3 | 3 | 3 | 3 |
| OTC Side | | | | | | |
| Adhesion | 1 | 2 | 2 | 3 | 5 | 4 |
| Transfer | 1 | 2 | 2 | 3 | 5 | 4 |
| Retention | 4 | 2 | 2 | 2 | 4 | 3 |
| Entire Device | | | Not Liquid Dependent | | | |
| Shape Memory | 4 | 4 | 5 | 5 | 4 | 4 |
| Finger Feel | 4 | 4 | 5 | 5 | 4 | 4 |
| Tear Strength | 3 | 3 | 5 | 5 | 4 | 4 |
| Color Contrast | 3 | 3 | 3 | 3 | 3 | 3 |

LSR was superior in non-liquid dependent characteristics and better than Enflex in terms of drop adhesion, but worse than Hytrel in that regard.

Test 6. Adhesion time for all Embodiments: The adhesion time for all embodiments was tested using Blink Tears and Azopt, an ophthalmic medicine, using both 30 μL Land 50 μL drop sizes. The Blink trials were run once on the Rx sides and twice on the OTC sides. Azopt was in short supply and was only tried once on the RX sides. Table 1 provides a more complete mechanical description of the embodiments, but salient features are repeated in the table 6 below.

Although there is some lack of reproducibility, the trends are clear. In particular, a 30 μL drop may adhere well to some embodiments while a 50 μL drop does not to those same embodiments.

Drop Tracings:

One may appreciate the challenge by inspection of the tracings of drops in FIGS. 16A-16L. The tracings were made from actual photomicrographs and are shown at about a 4× magnification. The 12 tracings show two drops sizes, 30 μL and 50 μL on embodiment no. 26 (designated an "RX" with a dam and a flat polished surface) and on embodiment no. 25 (designated an "OTC" with a flat textured surface circumscribed by a 0.012 in. (0.3 mm) high ring) at 0°, 90°, and 180° of rotation.

Figure 16A:
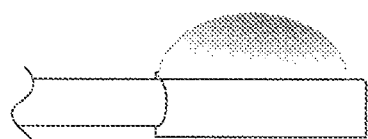
FIG. 16A is a tracing of a 30 μL drop on embodiment 26 at 0° rotation.
Figure 16D:
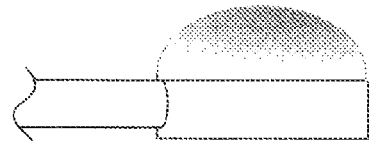
FIG. 16D is a tracing of a 50 μL drop on the same embodiment at 0°.
Figure 16B:
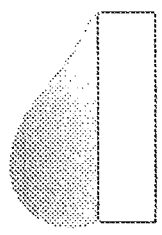
FIG. 16B is a tracing of a 30 μL drop on the same embodiment at 90°.
Figure 16E:
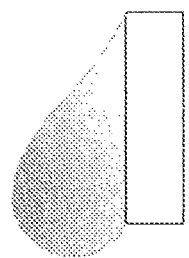
FIG. 16E is a tracing of a 50 μL drop on the same embodiment at 90°.
Figure 16C:
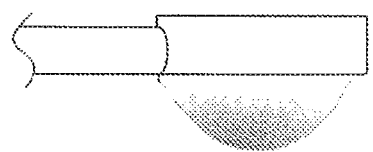
FIG. 16C is a tracing of a 30 μL drop on the same embodiment at 180°.

FIGS. 16A-16C show a 30 μL drop on the Rx surface. One can see at 0° in FIG. 16A, that the drop makes a normal angle with the surface indicating that wetting is not substantial. FIG. 16B shows the drop still adhering at 90° The 180° rotation, in FIG. 16C, is not normally required to use the device, but is included for completeness.

Figure 16F:
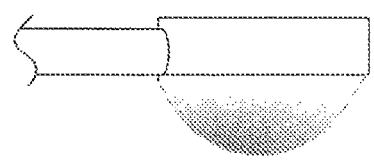
FIG. 16F is a tracing of a 50 μL drop on the same embodiment at 180°.

FIGS. 16D-16F show similar results for a 50 μL drop. Here, in the 0° tracing, it has expanded to the edge of the surface. (The dam, not shown, should constrain the larger drop to the tip of the device.) The 90° tracing illustrates the challenge in retaining a drop.

Figure 16G:
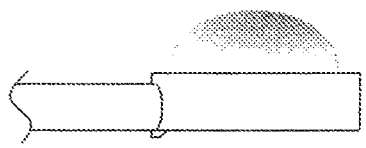
FIG. 16G is a tracing of a 30 μL drop on embodiment no. 25 at 0° rotation.
Figure 16J:
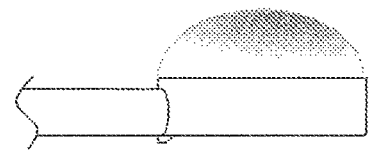
FIG. 16J is a tracing of a 50 μL drop on the same embodiment at 0°.
Figure 16H:
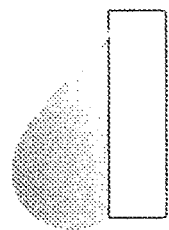
FIG. 16H is a tracing of a 30 μL drop on the same embodiment at 90°.
Figure 16K:
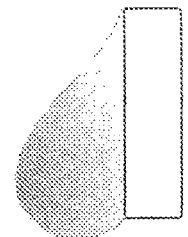
FIG. 16K is a tracing of a 50 μL drop on the same embodiment at 90°.
Figure 16I:
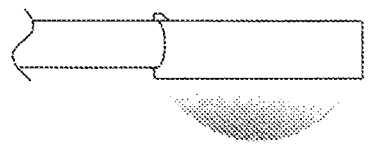
FIG. 16I is a tracing of a 30 μL drop on the same embodiment at 180°.

FIGS. 16G-16I show a 30 μL drop on an OTC surface surrounded by a ring. Because the drop is small enough, the ring is not touched until rotated 90° in FIG. 16H. There, the drop appears to be more precariously held than without the ring in FIG. 16B.

TABLE 6

Adhesion Tests for 26 Embodiments

| Emb. | Material | OTC/Rx | FIG. | Description | Other, if any Drop Size (μL): | Blink #1 30 | Blink #1 50 | Blink #2 30 | Blink #2 50 | Azopt 30 | Azopt 50 |
|---|---|---|---|---|---|---|---|---|---|---|---|
| 1 | LSR | — | 10A,B | Flat | .218 (5.5 mm) Tip | 0 | 0 | 0 | 0 | — | — |
| 2 | LSR | — | 11A,B | Cup | .218 (5.5 mm) Tip | 0 | 0 | 0 | 0 | — | — |
| 3 | LSR | — | 12A,B | Dome | | 0 | 0 | 0 | 0 | — | — |
| 4 | LSR | — | 12C,D | Flat | | 0 | 0 | 0 | 0 | — | — |
| 5 | Santoprene | OTC | 13A,B | Dome | Ring | 40 | 28 | 60 | 0 | — | — |
| 6 | Santoprene | Rx | 13C,D | " | | 25 | 0 | — | — | 60 | 0 |
| 7 | Vistamaxx | OTC | 13A,B | " | Ring | 60 | 0 | 60 | 0 | — | — |
| 8 | Vistamaxx | Rx | 13C,D | " | | 40 | 0 | — | — | 60 | 0 |
| 9 | C-Flex | OTC | 13A,B | " | Ring | 0 | 0 | 0 | 0 | — | — |
| 10 | C-Flex | Rx | 13C,D | " | | 0 | 0 | — | — | 7 | 0 |
| 11 | LSR-Parylene | OTC | 13A,B | " | Ring | 0 | 0 | 0 | 0 | — | — |
| 12 | LSR-Parylene | Rx | 13C,D | " | | 0 | 0 | — | — | 10 | 0 |
| 13 | Enflex | OTC | 13A,B | " | Ring | 0 | 0 | 60 | 0 | — | — |
| 14 | Enflex | Rx | 13C,D | " | | 0 | 0 | — | — | 25 | 0 |
| 15 | Hytrel | OTC | 13A,B | " | Ring | 0 | 0 | 0 | 0 | — | — |
| 16 | Hytrel | Rx | 13C,D | " | | 0 | 0 | — | — | 44 | 0 |
| 17 | Hytrel | OTC | 13A,B | " | Ring | 60 | 37 | 3 | 0 | — | — |
| 18 | Hytrel | Rx | 13C,D | " | | 2 | 0 | — | — | 60 | 0 |
| 19 | Hytrel | OTC | 13A,B | " | Ring | 60 | 25 | 10 | 0 | — | — |
| 20 | Hytrel | Rx | 13C,D | " | | 3 | 0 | — | — | 60 | 0 |
| 21 | Hytrel | OTC | 14A,B | Flat | Ring | 60 | 60 | 60 | 0 | — | — |
| 22 | Hytrel | Rx | 14C,D | " | Textured | 60 | 60 | — | — | 60 | 0 |
| 23 | Hytrel | OTC | 14A,B | " | Ring | 60 | 60 | 60 | 0 | — | — |
| 24 | Hytrel | Rx | 14C,D | " | Polished | 60 | 60 | — | — | 60 | 0 |
| 25 | Hytrel | OTC | 15A,B | " | .012 (0.3 mm) Ring | 60 | 60 | 60 | 60 | — | — |
| 26 | Hytrel | Rx | 15C,D | " | Polished | 60 | 60 | — | — | 60 | 0 |

Figure 16L:
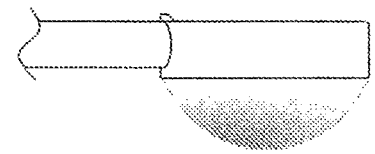
FIG. 16L is a tracing of a 50 μL drop on the same embodiment at 180°.

FIGS. 16J-16L repeat the previous figures with a 50 μL drop. Here, in FIG. 16J, it does expand to the ring. In FIG. 16K, the ring appears to slightly improve the precarious situation shown in FIG. 16E.

DEFINITIONS

In the claims, the following definitions are intended:

"Soft pliable" includes most elastomers, but excludes hard plastics such as polycarbonate, polystyrene and rigid metals.

"Reservoir-less" means, as shown in the figures, there are no internal reservoirs capable of holding drops of a size effective for holding eye medicaments. Normally, the device is solid, but internal voids are not excluded.

A "liquid drop retainer area" is an area to which a liquid drop adheres.

"Continuous surface" is meant to exclude cotton swabs, sponge-like materials, meshes and the like.

"Generally flat" is illustrated by FIG. 14B, as opposed to FIG. 11B which shows a concave cup and FIG. 1B which shows a convex dome.

The benefits of 35 U.S.C. 112(f) is invoked only by "means for" as in claim 25. The preferred means is illustrated by FIGS. 15A-15D, the attendant discussion, and equivalents.

What is claimed is:

1. An eye drop transfer system for transferring an ophthalmic medicament to an eye of a patient, said system comprising:
   a transfer device, comprising
      a grip portion, and
      a disc-shaped droplet retainer portion connected to the grip portion and positioned opposite the grip portion at a distal most end of said device, the retainer portion having a first side and a second side opposite the first side; and
   a droplet of the ophthalmic medicament disposed on one of the first and second sides;
   wherein the device is formed of an elastomeric material, the first side includes a flat, textured surface with a raised peripheral ring, and the second side includes a completely flat, polished surface.

2. The eye drop transfer system of claim 1 in which at least one of the first and second sides is circular.

3. The eye drop transfer system of claim 2 in which the at least one of the first and second sides has a diameter in the range of about ¼ inch to about 9/32 inch.

4. The eye drop transfer system of claim 1 in which the raised ring has a height of about 0.008 to 0.012 inches.

5. The eye drop transfer system of claim 1, wherein the grip portion includes a pliable extension which narrows to a distal end and terminates in the retainer portion.

6. The eye drop transfer system of claim 5, wherein the grip portion further comprises a partial dam interposed between the retainer portion and the extension.

7. The eye drop system of claim 1, wherein at least a portion of said transfer device is formed at least in part from an elastomeric material having a flexural Young's modulus in the range of 0.01 to 0.1 GPa.

8. The eye drop transfer system of claim 1, wherein at least a portion of said transfer device is formed at least in part from an elastomeric material having a nominal hardness in the range of 30 Shore A to 30 Shore D.

9. An eye drop transfer device for transferring an ophthalmic medicament to an eye of a patient, said device comprising:
   a grip portion; and
   a disc-shaped droplet retainer portion connected to said grip portion and positioned opposite said grip portion at a distal most end of the device, the retainer portion having a first side and a second side opposite the first side;
   wherein the device is formed of an elastomeric material, the first side includes a flat, textured surface with a raised peripheral ring, and the second side includes a completely flat, polished surface.

10. The eye drop transfer device of claim 9 in which at least one of the first and second sides is circular.

11. The eye drop transfer device of claim 10 in which the at least one of the first and second sides has a diameter in the range of about ¼ inch to about 9/32 inch.

12. The eye drop transfer device of claim 9 in which the raised ring has a height of about 0.008 to 0.012 inches.

13. The eye drop transfer device of claim 9, wherein said grip portion includes a pliable extension which narrows to a particular distal end and terminates in said retainer portion.

14. The eye drop transfer device of claim 13, wherein said grip portion further comprises a partial dam interposed between said retainer portion and the extension.

15. The eye drop transfer device of claim 9, wherein at least a portion of the transfer device is formed at least in part from an elastomeric material having a flexural Young's modulus in the range of 0.01 to 0.1 GPa.

16. The eye drop transfer device of claim 9, wherein at least a portion of the transfer device is formed at least in part from an elastomeric material having a nominal hardness in the range of 30 Shore A to 30 Shore D.

* * * * *